United States Patent
Guedes et al.

(10) Patent No.: US 10,383,835 B2
(45) Date of Patent: Aug. 20, 2019

(54) TREATMENT OF INFLAMMATORY DISORDERS IN NON-HUMAN MAMMALS

(71) Applicant: The Regents of the University of California, Oakland, CA (US)

(72) Inventors: Alonso G. P. Guedes, Davis, CA (US); Bruce D. Hammock, Davis, CA (US); Christophe Morisseau, West Sacramento, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 624 days.

(21) Appl. No.: 14/384,910

(22) PCT Filed: Mar. 5, 2013

(86) PCT No.: PCT/US2013/029214
§ 371 (c)(1),
(2) Date: Nov. 21, 2014

(87) PCT Pub. No.: WO2013/138118
PCT Pub. Date: Sep. 19, 2013

(65) Prior Publication Data
US 2015/0017267 A1    Jan. 15, 2015

Related U.S. Application Data

(60) Provisional application No. 61/610,839, filed on Mar. 14, 2012.

(51) Int. Cl.
*A61K 31/196*    (2006.01)
*A61K 31/17*    (2006.01)
(Continued)

(52) U.S. Cl.
CPC .......... *A61K 31/196* (2013.01); *A61K 31/167* (2013.01); *A61K 31/17* (2013.01);
(Continued)

(58) Field of Classification Search
CPC ........ A61K 31/352; A61K 9/14; A61K 31/17; A61K 31/196; A61K 31/16; A61K 31/192;
(Continued)

(56) References Cited

U.S. PATENT DOCUMENTS

| 7,951,831 B2 | 5/2011 | Hammock et al. |
| 8,399,425 B2 | 3/2013 | Hammock et al. |

(Continued)

FOREIGN PATENT DOCUMENTS

| WO | WO 00/23060 A2 * | 4/2000 |
| WO | WO 2006/086108 A2 | 8/2006 |
| WO | WO 2007/022509 A2 | 2/2007 |

OTHER PUBLICATIONS

Inceoglu et al., Soluble epoxide hydrolase inhibition reveals novel biological functions of epoxyeicosatrienoic acids (EETs). Prostaglandins and other Lipid Mediators. 2007, 82:47-49.*

(Continued)

*Primary Examiner* — Lakshmi S Channavajjala
(74) *Attorney, Agent, or Firm* — Mintz, Levin, Cohn, Ferris, Glovsky and Popeo, P.C.

(57) ABSTRACT

The present invention relates to the prevention, reduction, inhibition and reversal of pain and inflammation in a non-human mammal by administration of an inhibitor of soluble epoxide hydrolase, as sole active agent or co-administered with other active agents.

2 Claims, 6 Drawing Sheets

Specification includes a Sequence Listing.

(51) Int. Cl.
| | |
|---|---|
| A61K 45/06 | (2006.01) |
| A61K 31/167 | (2006.01) |
| A61K 31/192 | (2006.01) |
| A61K 31/405 | (2006.01) |
| A61K 31/415 | (2006.01) |
| A61K 31/451 | (2006.01) |
| A61K 31/513 | (2006.01) |
| A61K 31/5415 | (2006.01) |
| A61K 31/603 | (2006.01) |
| A61K 31/197 | (2006.01) |
| A61K 31/4152 | (2006.01) |

(52) U.S. Cl.
CPC .......... *A61K 31/192* (2013.01); *A61K 31/197* (2013.01); *A61K 31/405* (2013.01); *A61K 31/415* (2013.01); *A61K 31/4152* (2013.01); *A61K 31/451* (2013.01); *A61K 31/513* (2013.01); *A61K 31/5415* (2013.01); *A61K 31/603* (2013.01); *A61K 45/06* (2013.01)

(58) Field of Classification Search
CPC ................ A61K 31/197; A61K 31/415; A61K 31/4152; A61K 31/451; A61K 31/513; A61K 31/5415; A61K 31/603; C07D 211/96; C07D 211/58
See application file for complete search history.

(56) References Cited

U.S. PATENT DOCUMENTS

| | | |
|---|---|---|
| 8,455,520 B2 | 6/2013 | Colletti et al. |
| 2005/0113409 A1* | 5/2005 | Connor ................ A61K 31/415 514/311 |
| 2007/0141182 A1* | 6/2007 | Niazi .................... A61K 31/19 424/755 |
| 2009/0023731 A1 | 1/2009 | Gless et al. |
| 2010/0197691 A1 | 8/2010 | Colletti et al. |
| 2010/0267807 A1 | 10/2010 | Hammock et al. |

OTHER PUBLICATIONS

Bundgaard. Design of prodrugs. 1985. Elsevier Science Publishers B. V. Design of prodrugs: Bioreversible derivatives for various functional groups and chemical entities. Chapter I. pp. 1-94. Feb. 1996.*
Banker et al. Modern Pharmaceutics, 3rd Edition, Marcel Dekker, Inc. Publisher. Revised and Expanded. B. Prodrugs. pp. 596, 451.*
Burger's Medicinal Chemistry and Drug Discovery. Wolff. Feb. 1995. 5th edition. vol. I: principles and practice. pp. 975-977.*
Schmelzer, K.R. et al.: "*Enhancement of antinociception by coadministration of nonsteroidal anti-inflammatory drugs and soluble epoxide hydrolase inhibitors*"; Proceedings of the National Academy of Sciences, Sep. 12, 2006, vol. 103, No. 37, pp. 13646-13651.
Supplementary European Search Report dated Feb. 12, 2016 regarding EP 13 76 1684.

* cited by examiner

TREATMENT OF INFLAMMATORY DISORDERS IN NON-HUMAN MAMMALS

CROSS-REFERENCE TO RELATED APPLICATIONS

This application is a 35 USC § 371 National Stage application of International Application No. PCT/US2013/029214 filed Mar. 5, 2013, now pending; which claims the benefit under 35 USC § 119(e) to U.S. Application Ser. No. 61/610,839 filed Mar. 14, 2012. The disclosure of each of the prior applications is considered part of and is incorporated by reference in the disclosure of this application.

STATEMENT OF GOVERNMENTAL SUPPORT

This invention was made with government support under Grant Nos. ES002710 and ES004699, awarded by the National Institutes of Health. The government has certain rights in the invention.

FIELD

The present invention relates to the prevention, reduction, inhibition and reversal of pain and inflammation in a non-human mammal by administration of an inhibitor of soluble epoxide hydrolase, as sole active agent or co-administered with other active agents.

BACKGROUND

Laminitis is an extremely painful condition of the foot in horses. Its pathophysiology remains poorly understood, but involves both vascular and inflammatory events within the hoof leading to disruption of the lamellar dermo-epidermal junction, impaired biomechanical function, pain and substantial suffering (Hood et al. 1993; Hood 1999; Sumano Lopez et al. 1999; Parks & O'Grady 2003; Driessen et al. 2010). Ischemia and inflammation in the early stages of laminitis likely cause neuronal injury that eventually shifts the acute inflammatory pain into a chronic syndrome with a prominent neuropathic component (Moalem & Tracey 2006; Peroni et al. 2006; Belknap et al. 2007; Jones et al. 2007). The precise timing and nature of these events remain elusive. The response to treatment can be quite unpredictable. Such complexity makes pain management in horses with laminitis one of the biggest challenges in equine practice. Non-steroidal anti-inflammatory drugs (NSAID) are the mainstay analgesics for this condition. However, abridged efficacy against neuropathic pain and risks of dose-dependent gastrointestinal and renal adverse effects are significant limitations of these compounds (Sumano Lopez et al. 1999; Taylor et al. 2002; Driessen et al. 2010). These constraints often leave euthanasia as the only humane alternative to alleviate pain and suffering in affected horses (Driessen et al. 2010). This clearly underscores the need for the development of more efficacious and safer analgesics.

The oxidative metabolism of polyunsaturated fatty acids (PUFAs) such as arachidonic acid (ARA), docosahexaenoic acid (DHA), eicosapentaenoic acid (EPA) and linoleic acid (LNA) produces potent inflammatory mediators. Most of the analgesic research and drug development has focused on inhibiting ARA derivatives formed by cyclooxygenases (COX) (Tokuyama & Nakamoto 2011). Cytochrome P450 enzymes mediate another critical yet relatively unexplored pathway of PUFAs metabolism. This pathway transforms PUFAs into various biologically active compounds, including epoxy-fatty acids (EFAs or epoxides), such as epoxy-eicosatrienoic acids (EETs), or hydroxyl derivatives, such as hydroxy-eicosatetraenoic acids (HETEs) (Wagner et al. 2011b). These EFAs have multiple biological activities including the modulation of inflammation and nociceptive signaling (Murakami 2011). The biological activity of these epoxides is restricted as they are metabolized to the corresponding diols by the soluble epoxide hydrolases (sEH) (Wagner et al. 2011a). This has been confirmed with the development and use of sEH inhibitors (sEHis) (Morisseau & Hammock 2005; Hwang et al. 2007) in conditions involving several body systems and functions (Revermann 2010). The microsomal (mEH) and soluble (sEH) epoxide hydrolases were first thought to play a role in xenobiotic metabolism in mammalian tissues. Even though this is largely true for mEH, sEH has a minor role in xenobiotic metabolism. The major function of sEH is the degradation of endogenous lipid metabolites (Morisseau & Hammock 2008; Decker et al. 2009).

SUMMARY

In one aspect, the invention provides methods of preventing, ameliorating, delaying the progression and/or reversing the progression of an inflammatory condition in a non-human mammal. In some embodiments, the methods comprise administering to the mammal an agent that increases EETs (e.g., an inhibitor of soluble epoxide hydrolase (sEH), an EET, an epoxygenated fatty acid, and mixtures thereof).

In another aspect, the invention provides methods of enhancing or maintaining the anti-inflammatory efficacy and/or anti nociceptive efficacy and reducing undesirable side effects of a NSAID in a non-human mammal. In some embodiments, the methods comprise co-administering to the non-human mammal in need thereof the NSAID and an agent that increases EETs (e.g., an inhibitor of sEH, an EET, an epoxygenated fatty acid, and mixtures thereof) and the anti-inflammatory agent. One or both of the NSAID and the agent that increases EETs can be administered in a sub-therapeutic amount.

In another aspect, the invention provides methods of preventing, ameliorating, delaying the progression and/or reversing the progression of chronic pain in a non-human mammal. In some embodiments, the methods comprise administering to the mammal an agent that increases EETs (e.g., an inhibitor of sEH, an EET, an epoxygenated fatty acid, and mixtures thereof).

In another aspect, the invention provides methods of enhancing or maintaining the anti-nociceptive efficacy on chronic pain and/or neuropathic pain and reducing undesirable side effects of an active agent selected from the group consisting of NSAIDS, phosphodiesterase inhibitors, Gamma-aminobutyric Acid (GABA) analogs, N-methyl-D-aspartate receptor antagonists, opioids and sodium channel blockers, or analogs or pro-drugs thereof, in a non-human mammal, comprising co-administering to the non-human mammal in need thereof an inhibitor of soluble epoxide hydrolase and the active agent, or an analog or pro-drug thereof. One or both of the active agent and the inhibitor of soluble epoxide hydrolase can be administered in a sub-therapeutic amount.

In some embodiments, the non-human mammal is canine, feline, equine, bovine, ovine or porcine. In some embodiments, the non-human mammal is canine or feline. In some embodiments, the non-human mammal is an ungulate (e.g., equine, bovine, ovine or porcine). In some embodiments, the non-human mammal is equine. In some embodiments, the inflammatory condition is laminitis.

In some embodiments, the inflammatory condition is selected from the group consisting of injury and/or recovery from injury, surgery and/or recovery from surgery, hip dysplasia, osteoarthritis and tendonitis. In some embodiments, the non-human mammal is experiencing inflammatory and/or neuropathic pain, and/or any disease state or condition (e.g., post-surgical trauma) that is associated with inflammation and/or pain.

In another aspect, the invention provides methods for preventing, ameliorating, delaying the progression and/or reversing the progression of laminitis in an equine. In some embodiments, the methods comprise administering to the mammal an agent that increases EETs (e.g., an inhibitor of soluble epoxide hydrolase (sEH), an EET, an epoxygenated fatty acid, and mixtures thereof). In various embodiments, the agent that increases EETs is co-administered with an anti-inflammatory agent (e.g., an NSAID, a phosphodiesterase inhibitor) and/or a Gamma-aminobutyric Acid (GABA) analog and/or a sodium channel blocker (e.g., amantadine, gabapentin or pregabalin, lidocaine, or analogs or pro-drugs thereof).

In some embodiments, an inhibitor of sEH is administered. In some embodiments, the inhibitor of sEH comprises a primary pharmacophore selected from the group consisting of a urea, a carbamate, and an amide. In varying embodiments, the inhibitor of sEH comprises a cyclohexyl moiety, aromatic moiety, substituted aromatic moiety or alkyl moiety attached to the pharmacophore. In some embodiments, the inhibitor of sEH comprises a cyclohexyl ether moiety attached to the pharmacophore. In some embodiments, the inhibitor of sEH comprises a phenyl ether or piperidine moiety attached to the pharmacophore. In some embodiments, the inhibitor of sEH comprises a polyether secondary pharmacophore. In some embodiments, the inhibitor of sEH has an IC50 of less than about 100 μM, for example, an $IC_{50}$ of less than about 75 μM, 50 μM, 25 μM, 10 μM, 1 μM, 100 nM, 10 nM or 1 nM. As appropriate, the IC50 for inhibition of sEH is determined with respect to the sEH enzyme from the same species as the non-human mammal receiving the inhibitor of sEH (e.g., IC50 for inhibition of sEH is determined with respect to the species subject to treatment, e.g., with respect to the sEH enzyme from equine, bovine, ovine, porcine, canine, feline, etc., for subjects who are equine, bovine, ovine, porcine, canine, feline, respectively).

In some embodiments, the inhibitor of sEH is selected from the group consisting of:
a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxy]pentyl]}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (tAUCB; compound 1471);
f) cis-4-[4-(3-Adamantan-1-yl-ureido)-cyclohexyloxy]-benzoic acid (cAUCB; compound 1686);
g) 1-(1-methylsulfonyl-piperidin-4-yl)-3-(4-trifluoromethoxy-phenyl)-urea (TUPS; compound 1709);
h) trans-4-{4-[3-(4-Trifluoromethoxy-phenyl)-ureido]-cyclohexyloxy}-benzoic acid (tTUCB; compound 1728);
i) 1-trifluoromethoxyphenyl-3-(1-propionylpiperidin-4-yl) urea (TPPU; compound 1770);
j) 1-(1-ethylsulfonyl-piperidin-4-yl)-3-(4-trifluoromethoxy-phenyl)-urea (TUPSE; compound 2213)
k) 1-(1-(cyclopropanecarbonyl)piperidin-4-yl)-3-(4-(trifluoromethoxy)phenyl)urea (CPTU; compound 2214);
l) trans-N-methyl-4-[4-(3-Adamantan-1-yl-ureido)-cyclohexyloxy]-benzamide (tMAUCB; compound 2225)
m) trans-N-methyl-4-[4-((3-trifluoromethyl-4-chlorophenyl)-ureido)-cyclohexyloxy]-benzamide (tMTCUCB; compound 2226);
n) cis-N-methyl-4-{4-[3-(4-trifluoromethoxy-phenyl)-ureido]-cyclohexyloxy}-benzamide (cMTUCB; compound 2228); and
o) 1-cycloheptyl-3-(3-(1,5-diphenyl-1H-pyrazol-3-yl) propyl)urea (HDP3U; compound 2247).

In some embodiments, the inhibitor of sEH is selected from the group consisting of:
a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxy]pentyl]}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (tAUCB; compound 1471);
f) cis-4-[4-(3-Adamantan-1-yl-ureido)-cyclohexyloxy]-benzoic acid (cAUCB; compound 1686);
g) trans-4-{4-[3-(4-Trifluoromethoxy-phenyl)-ureido]-cyclohexyloxy}-benzoic acid (tTUCB; compound 1728);
h) trans-N-methyl-4-[4-(3-Adamantan-1-yl-ureido)-cyclohexyloxy]-benzamide (tMAUCB; compound 2225)
i) trans-N-methyl-4-[4-((3-trifluoromethyl-4-chlorophenyl)-ureido)-cyclohexyloxy]-benzamide (tMTCUCB; compound 2226);
j) cis-N-methyl-4-{4-[3-(4-trifluoromethoxy-phenyl)-ureido]-cyclohexyloxy}-benzamide (cMTUCB; compound 2228); and
k) 1-cycloheptyl-3-(3-(1,5-diphenyl-1H-pyrazol-3-yl) propyl)urea (HDP3U; compound 2247).

In some embodiments, the inhibitor of sEH is selected from the group consisting of:
a) trans-4-[4-(3-Adamantan-1-yl-ureido)-cyclohexyloxy]-benzoic acid (tAUCB; compound 1471);
b) 4-{4-[3-(4-Trifluoromethoxy-phenyl)-ureido]-cyclohexyloxy}-benzoic acid (tTUCB; compound 1728);
c) 1-trifluoromethoxyphenyl-3-(1-propionylpiperidin-4-yl) urea (TPPU; compound 1770);
d) trans-2-(4-(4-(3-(4-trifluoromethoxy-phenyl)-ureido)-cyclohexyloxy)-benzamido)-acetic acid (compound 2283);
e) N-(methylsulfonyl)-4-(trans-4-(3-(4-trifluoromethoxy-phenyl)-ureido)-cyclohexyloxy)-benzamide (compound 2728);
f) 1-(trans-4-(4-(1H-tetrazol-5-yl)-phenoxy)-cyclohexyl)-3-(4-(trifluoromethoxy)-phenyl)-urea (compound 2806);
g) 4-(trans-4-(3-(2-fluorophenyl)-ureido)-cyclohexyloxy)-benzoic acid (compound 2736);
h) 4-(4-(3-(4-(trifluoromethoxy)-phenyl)-ureido)-phenoxy)-benzoic acid (compound 2803);
i) 4-(3-fluoro-4-(3-(4-(trifluoromethoxy)-phenyl)-ureido)-phenoxy)-benzoic acid (compound 2807);
j) N-hydroxy-4-(trans-4-(3-(4-(trifluoromethoxy)-phenyl)-ureido)-cyclohexyloxy)-benzamide (compound 2761);
k) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);

l) 1-(4-oxocyclohexyl)-3-(4-(trifluoromethoxy)-phenyl)-urea (compound 2809);

m) methyl 4-(4-(3-(4-(trifluoromethoxy)-phenyl)-ureido)-cyclohexylamino)-benzoate (compound 2804);

n) 1-(4-(pyrimidin-2-yloxy)-cyclohexyl)-3-(4-(trifluoromethoxy)-phenyl)-urea (compound 2810); and o) 4-(trans-4-(3-(4-(difluoromethoxy)-phenyl)-ureido)-cyclohexyloxy)-benzoic acid (compound 2805).

In some embodiments, a non-steroidal anti-inflammatory drug (NSAID) was previously administered and the NSAID did not prevent, sufficiently ameliorate, delay or reverse progression of the inflammatory and/or neuropathic pain condition.

In some embodiments, the agent that increases EETs (e.g., an inhibitor of sEH, an EET, an epoxygenated fatty acid, and mixtures thereof) is co-administered with one or more NSAIDs. In some embodiments, the NSAID inhibits one or more enzymes selected from the group consisting of cyclooxygenase ("COX")-1, COX-2, and 5 lipoxygenase ("5-LOX"). In some embodiments, the NSAID is selected from the group consisting of flunixin meglumine, phenylbutazone, aspirin, acetaminophen, diclofenac potassium, diclofenac sodium, diclofenac sodium with misoprostol, diflunisal, dipyrone, ketorolac, etodolac, tepoxalin, fenoprofen calcium, flurbiprofen, ibuprofen, indomethacin, ketoprofen, vedaprofen, meclofenamate sodium, mefenamic acid, tolfenamic acid, meloxicam, carprofen, nabumetone, naproxen sodium, piroxicam, tolmetin sodium, magnesium salicylate, choline salicylate, salsalate, sodium salicylate, alkyl salicylate and disalicylate. In some embodiments, the NSAID is a selective inhibitor of COX-2. In some embodiments, the selective inhibitor of COX-2 is selected from the group consisting of celecoxib, valdecoxib, lumiracoxib, etoricoxib, rofecoxib, robenacoxib, deracoxib and firocoxib. In some embodiments, one or both of the inhibitor of sEH and the NSAID are administered in a sub-therapeutic amount. In some embodiments, a dual inhibitor of sEH and COX-2 is administered.

In some embodiments, an active agent selected from the group consisting of phosphodiesterase inhibitors, Gamma-aminobutyric Acid (GABA) analogs, N-methyl-D-aspartate receptor antagonists, opioids and sodium channel blockers, or analogs or pro-drugs thereof, was previously administered and the active agent did not prevent, sufficiently ameliorate, delay or reverse the inflammatory and/or neuropathic pain condition. In some embodiments, a Gamma-aminobutyric Acid (GABA) analog (e.g., gabapentin or pregabalin, or analogs or pro-drugs thereof) was previously administered and the GABA analog did not prevent, ameliorate, delay or reverse the inflammatory and/or neuropathic pain condition.

In some embodiments, the inhibitor of sEH is co-administered with an active agent selected from the group consisting of NSAIDS, phosphodiesterase inhibitors, Gamma-aminobutyric Acid (GABA) analogs, N-methyl-D-aspartate receptor antagonists, opioids and sodium channel blockers, or analogs or pro-drugs thereof. One or both of the inhibitor of sEH and the active agent can be administered in a sub-therapeutic amount.

In some embodiments, the inhibitor of sEH is co-administered with a Gamma-aminobutyric Acid (GABA) analog, or analogs or pro-drugs thereof. In some embodiments, the GABA analog is selected from the group consisting of gabapentin, pregabalin, and analogs or pro-drugs thereof. In some embodiments, one or both of the inhibitor of sEH and the Gamma-aminobutyric Acid (GABA) analog (e.g., gabapentin or pregabalin, or analogs or pro-drugs thereof), are administered in a sub-therapeutic amount.

In some embodiments, the inhibitor of sEH is co-administered with an N-methyl-D-aspartate receptor antagonist, or an analog or pro-drug thereof. In some embodiments, the N-methyl-D-aspartate receptor antagonist is selected from the group consisting of: AP5 (APV, R-2-amino-5-phosphonopentanoate); AP7 (2-amino-7-phosphonoheptanoic acid); CPPene (3-[(R)-2-carboxypiperazin-4-yl]-prop-2-enyl-1-phosphonic acid); Selfotel; Amantadine; Dextrallorphan; Dextromethorphan; Dextrorphan; Dizocilpine (MK-801); Eticyclidine; Gacyclidine; Ibogaine; Memantine; Methoxetamine; Nitrous oxide; Phencyclidine; Rolicyclidine; Tenocyclidine; Methoxydine; Tiletamine; Xenon; Neramexane; Eliprodil; Etoxadrol; Dexoxadrol; NEFA ((4aR,9aS)-N-Ethyl-4,4a,9,9a-tetrahydro-1H-fluoren-4a-amine); Remacemide; Delucemine; 8a-Phenyldecahydroquinoline (8A-PDHQ); Aptiganel (Cerestat, CNS-1102); Dexanabinol (HU-211); Rhynchophylline; and Ketamine.

In some embodiments, the inhibitor of sEH is co-administered with an opioid, or an analog or pro-drug thereof. In some embodiments, the opioid is selected from the group consisting of morphine, codeine, thebaine, heroin, hydromorphone, hydrocodone, oxycodone, oxymorphone, desomorphine, nicomorphine, dipropanoylmorphine, benzylmorphine, ethylmorphine, buprenorphine, fentanyl, pethidine, methadone, tramadol and dextropropoxyphene.

In some embodiments, the inhibitor of sEH is co-administered with a sodium channel blockers, or an analog or pro-drug thereof. In some embodiments, the sodium channel blocker is selected from the group consisting of tetrodotoxin (TTX), saxitoxin (STX), Benzocaine, Chloroprocaine, Cocaine, Cyclomethycaine, Dimethocaine/Larocaine, Piperocaine, Propoxycaine, Procaine/Novocaine, Proparacaine, Tetracaine/Amethocaine, Articaine, Bupivacaine, Cinchocaine/Dibucaine, Etidocaine, Levobupivacaine, Lidocaine/Lignocaine, Mepivacaine, Prilocaine, Ropivacaine, Trimecaine, and Lidocaine/prilocaine (EMLA), quinidine, procainamide, disopryamide, tocainide, mexiletine, flecainide, propafenone, moricizine, Carbamazepine, Phenytoin, Fosphenytoin, Oxcarbazepine, Lamotrigine, and Zonisamide.

In some embodiments, the inhibitor of sEH is co-administered with a phosphodiesterase inhibitor, or an analog or pro-drug thereof. In varying embodiments, the phosphodiesterase inhibitor is selected from the group consisting of rolipram, roflumilast, cilomilast, ariflo, HT0712, ibudilast, mesembrine, cilostamide, enoxamone, milrinone, siguazodan, BRL-50481, sildenafil, zaprinast, tadalafil, udenafil, avanafil and vardenafil.

In various embodiments, the one or more of the inhibitor of sEH and the active agent selected from the group consisting of phosphodiesterase inhibitors, Gamma-aminobutyric Acid (GABA) analogs, N methyl-D-aspartate receptor antagonists, opioids and sodium channel blockers, or analogs or pro-drugs thereof, are administered in a sub-therapeutic amount.

Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") and the corresponding epoxides of 18:2 omega-6 and omega-3 lipids such as EPA and DHA are biomediators synthesized by cytochrome P450 epoxygenases. As discussed further in a separate section below, while the use of unmodified EETs is the most preferred, derivatives of EETs, such as amides and esters (both natural and synthetic), EET analogs, and EET optical isomers can all be used in the methods, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides. The addition of water to the epoxides results in the corresponding 1,2-diols (Hammock, B. D. et al., in Comprehensive Toxicology: Biotransformation (Elsevier, New York), pp. 283-305 (1997); Oesch, F. Xenobiotica 3:305-340 (1972)). Four principal EH's are known: leukotriene epoxide hydrolase, cholesterol epoxide hydrolase, microsomal EH ("mEH"), and soluble EH ("sEH," EH2, previously called cytosolic EH). A mammalian gene, message, protein and activity for EH3 has been described and a gene for EH3. The leukotriene EH acts on leukotriene A4, whereas the cholesterol EH hydrates compounds related to the 5,6-epoxide of cholesterol. The microsomal epoxide hydrolase metabolizes mono-substituted, 1,1-disubstituted, cis-1,2-disubstituted epoxides and epoxides on cyclic systems to their corresponding diols. Because of its broad substrate specificity, this enzyme is thought to play a significant role in ameliorating epoxide toxicity. Reactions of detoxification typically decrease the hydrophobicity of a compound, resulting in a more polar and thereby excretable substance. EH3 appears to have very tissue limited distribution but does metabolize fatty acid epoxides.

"Soluble epoxide hydrolase" ("sEH") is an epoxide hydrolase which in many cell types converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). NCBI Entrez Nucleotide accession number L05779 sets forth the nucleic acid sequence encoding the protein, as well as the 5' untranslated region and the 3' untranslated region. The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Soluble EH is only very distantly related to mEH and hydrates a wide range of epoxides not on cyclic systems. In contrast to the role played in the degradation of potential toxic epoxides by mEH, sEH is believed to play a role in the formation or degradation of endogenous chemical mediators. Unless otherwise specified, as used herein, the terms "soluble epoxide hydrolase" and "sEH" refer to human sEH.

Unless otherwise specified, as used herein, the terms "sEH inhibitor" (also abbreviated as "sEHi") or "inhibitor of sEH" refer to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses pro-drugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

"COX" is an abbreviation for "cyclo-oxygenase." Several COX enzymes have been identified. Two isozymes, COX-1 and COX-2, are recognized as of clinical significance, with COX-1 considered to be constitutively expressed and COX-2 considered to be inducible and more prevalent at sites of inflammation. See, e.g., Hawkey, Best Pract Res Clin Gastroenterol. 15(5):801-20 (2001).

As used herein, a "COX-1 inhibitor" denotes an agent that inhibits COX-1 more than it inhibits COX-2, while a "COX-2 inhibitor" denotes an agent that inhibits COX-2 more than it inhibits COX-1. All current non-steroidal anti-inflammatory drugs (NSAIDs) inhibit both COX-1 and COX-2, but most tend to inhibit the two isoforms to different degrees. Since both enzymes tend to be inhibited together to some degree, one can consider an inhibitor of either enzyme to be "COX inhibitor".

"LOX" is an abbreviation for "lipoxygenase." Several LOX enzymes have been identified. Arachidonate 5-lipoxygenase ("5-LOX", EC 1.13.11.34) is involved in the production of pro-inflammatory mediators. Arachidonate 12-lipoxygenase ("12-LOX", EC 1.13.11.31) and arachidonate 15-lipoxygenase ("15-LOX", EC 1.13.11.33) form trihydroxytetraenes known as "lipoxins" ("lipoxygenase interaction products") from arachidonic acid. Lipoxins act as local anti-inflammatory agents.

"5-lipoxygenase activating protein," or "FLAP," is a protein required before 5-LOX can become catalytically active. Inhibiting FLAP activity reduces or prevents 5-LOX activation, decreasing the biosynthesis of leukotrienes.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

The term "therapeutically effective amount" refers to that amount of the compound being administered sufficient to prevent or decrease the development of one or more of the symptoms of the disease, condition or disorder being treated (e.g., pain and/or inflammation).

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Sub-therapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic and/or anti-inflammatory effects), or that quantitatively is less than the established therapeutic dose for that particular pharmacological agent (e.g., as published in a reference consulted by a person of skill, for example, doses for a pharmacological agent published in the Physicians' Desk Reference, 65th Ed., 2011, Thomson Healthcare or Brunton, et al., Goodman & Gilman's The Pharmacological Basis of Therapeutics, 12th edition, 2010, McGraw-Hill Professional). A "sub-therapeutic dose" can be defined in relative terms (i.e., as a percentage amount (less than 100%) of the amount of pharmacologically active agent conventionally administered). For example, a sub-therapeutic dose amount can be about 1% to about 75% of the amount of pharmacologically active agent conventionally administered. In some embodiments, a sub-therapeutic dose can be about 75%, 50%, 30%, 25%, 20%, 10% or less, than the amount of pharmacologically active agent conventionally administered.

The term "analgesic amount" refers to that amount of the compound being administered sufficient to prevent or decrease pain in a subject under treatment.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, University of the Sciences in Philadelphia, Eds., 21$^{st}$ Ed., Lippencott Williams & Wilkins (2005).

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering agent (e.g., an agent that increases EETs (e.g., an inhibitor of sEH, an EET, an epoxygenated fatty acid, and mixtures thereof), optionally with an anti-inflammatory agent and/or an analgesic agent) to a mammal so that the agent is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administration" refers to the presence of both active agents in the blood at the same time. Active agents that are co-administered can be delivered concurrently (i.e., at the same time) or sequentially.

The terms "patient," "subject" or "individual" interchangeably refers to a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The terms "inhibiting," "reducing," "decreasing" refers to inhibiting the pain and/or inflammation in a non-human mammalian subject by a measurable amount using any method known in the art. For example, inflammation is inhibited, reduced or decreased if an indicator of inflammation, e.g., swelling, blood levels of prostaglandin PGE2, is at least about 10%, 20%, 30%, 50%, 80%, or 100% reduced, e.g., in comparison to the same inflammatory indicator prior to administration of an agent that increases EETs (e.g., an inhibitor of sEH, an EET, an epoxygenated fatty acid, and mixtures thereof). In some embodiments, the pain and/or inflammation is inhibited, reduced or decreased by at least about 1-fold, 2-fold, 3-fold, 4-fold, or more in comparison to the pain and/or inflammation prior to administration of the agent that increases EETs (e.g., an inhibitor of sEH, an EET, an epoxygenated fatty acid, and mixtures thereof). Indicators of pain and/or inflammation can also be qualitative. For example, pain may be indicated by a reflexive retraction in response to touch and/or an unwillingness or inability to bear weight, e.g., by a limb bearing a painful or inflamed lesion.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., an agent that increases EETs (e.g., an inhibitor of sEH, an EET, an epoxygenated fatty acid, and mixtures thereof) and/or an anti-inflammatory agent.

As used herein, the term "alkyl" refers to a saturated hydrocarbon radical which may be straight-chain or branched-chain (for example, ethyl, isopropyl, t-amyl, or 2,5-dimethylhexyl). This definition applies both when the term is used alone and when it is used as part of a compound term, such as "hydroxyalkyl," "haloalkyl," "arylalkyl," "alkylamino" and similar terms. In some embodiments, alkyl groups are those containing 1 to 24 carbon atoms. All numerical ranges in this specification and claims are intended to be inclusive of their upper and lower limits.

Additionally, the alkyl and heteroalkyl groups may be attached to other moieties at any position on the alkyl or heteroalkyl radical which would otherwise be occupied by a hydrogen atom (such as, for example, 2-pentyl, 2-methylpent-1-yl and 2-propyloxy). Divalent alkyl groups may be referred to as "alkylene," and divalent heteroalkyl groups may be referred to as "heteroalkylene," such as those groups used as linkers in the present invention. The alkyl, alkylene, and heteroalkylene moieties may also be optionally substituted with halogen atoms, or other groups such as oxo, cyano, nitro, alkyl, alkylamino, carboxyl, hydroxyl, alkoxy, aryloxy, and the like.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, flouromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

The terms "cycloalkyl" and "cycloalkylene" refer to a saturated hydrocarbon ring and includes bicyclic and polycyclic rings. Similarly, cycloalkyl and cycloalkylene groups having a heteroatom (e.g. N, O or S) in place of a carbon ring atom may be referred to as "heterocycloalkyl" and "heterocycloalkylene," respectively. Examples of cycloalkyl and heterocycloalkyl groups are, for example, cyclohexyl, norbornyl, adamantyl, morpholinyl, thiomorpholinyl, dioxothiomorpholinyl, and the like. The cycloalkyl and heterocycloalkyl moieties may also be optionally substituted with halogen atoms, or other groups such as nitro, alkyl, alkylamino, carboxyl, alkoxy, aryloxy and the like. In some embodiments, cycloalkyl and cycloalkylene moieties are those having 3 to 12 carbon atoms in the ring (e.g., cyclohexyl, cyclooctyl, norbornyl, adamantyl, and the like). In some embodiments, heterocycloalkyl and heterocycloalkylene moieties are those having 1 to 3 hetero atoms in the ring (e.g., morpholinyl, thiomorpholinyl, dioxothiomorpholinyl, piperidinyl and the like). Additionally, the term "(cycloalkyl)alkyl" refers to a group having a cycloalkyl moiety attached to an alkyl moiety. Examples are cyclohexylmethyl, cyclohexylethyl and cyclopentylpropyl.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears an oxygen substituent which is capable of covalent attachment to another hydrocarbon radical (such as, for example, methoxy, ethoxy and t-butoxy).

The term "aryl" refers to an aromatic carbocyclic substituent which may be a single ring or multiple rings which are fused together, linked covalently or linked to a common group such as an ethylene or methylene moiety. Similarly, aryl groups having a heteroatom (e.g. N, O or S) in place of a carbon ring atom are referred to as "heteroaryl". Examples of aryl and heteroaryl groups are, for example, phenyl, naphthyl, biphenyl, diphenylmethyl, thienyl, pyridyl and quinoxalyl. The aryl and heteroaryl moieties may also be optionally substituted with halogen atoms, or other groups such as nitro, alkyl, alkylamino, carboxyl, alkoxy, phenoxy and the like. Additionally, the aryl and heteroaryl groups may be attached to other moieties at any position on the aryl or heteroaryl radical which would otherwise be occupied by a hydrogen atom (such as, for example, 2-pyridyl, 3-pyridyl and 4-pyridyl). Divalent aryl groups are "arylene", and divalent heteroaryl groups are referred to as "heteroarylene" such as those groups used as linkers in the present invention.

The terms "arylalkyl" and "alkylaryl", "refer to an aryl radical attached directly to an alkyl group. Likewise, the terms "arylalkenyl" and "aryloxyalkyl" refer to an alkenyl group, or an oxygen which is attached to an alkyl group, respectively. For brevity, aryl as part of a combined term as above, is meant to include heteroaryl as well. The term "aryloxy" refers to an aryl radical as described above which also bears an oxygen substituent which is capable of covalent attachment to another radical (such as, for example, phenoxy, naphthyloxy, and pyridyloxy).

The terms "halo" or "halogen," by themselves or as part of another substituent, mean, unless otherwise stated, a fluorine, chlorine, bromine, or iodine atom. Additionally, terms such as "haloalkyl," and "haloalkoxy" are meant to include monohaloalkyl(oxy) and polyhaloalkyl(oxy). For example, the term "$C_1$-$C_6$ haloalkyl" is mean to include trifluoromethyl, 2,2,2-trifluoroethyl, 4-chlorobutyl, 3-bromopropyl, and the like.

The term "hetero" as used in a "heteroatom-containing alkyl group" (a "heteroalkyl" group) or a "heteroatom-containing aryl group" (a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur or more than one non-carbon atom (e.g., sulfonamide). Similarly, the term "heteroalkyl" refers to an alkyl substituent that is heteroatom-containing, the terms "heterocyclic" "heterocycle" or "heterocyclyl" refer to a cyclic substituent or group that is heteroatom-containing and is either aromatic or non-aromatic. The terms "heteroaryl" and "heteroaromatic" respectively refer to "aryl" and "aromatic" substituents that are heteroatom-containing, and the like. The terms "heterocyclic" and "heterocyclyl" include the terms "heteroaryl" and "heteroaromatic". In some embodiments, heterocyclic moieties are those having 1 to 3 hetero atoms in the ring. Examples of heteroalkyl groups include alkoxy, alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing cyclic nonaromatic groups are morpholinyl, piperazinyl, piperidinyl, etc.

The term "substituted" refers to the replacement of an atom or a group of atoms of a compound with another atom or group of atoms. For example, an atom or a group of atoms may be substituted with one or more of the following substituents or groups: halo, nitro, $C_1$-$C_8$alkyl, $C_1$-$C_8$alkylamino, hydroxy$C_1$-$C_8$alkyl, halo$C_1$-$C_8$alkyl, carboxyl, hydroxyl, $C_1$-$C_8$alkoxy, $C_1$-$C_8$alkoxy$C_1$-$C_8$alkoxy, thio$C_1$-$C_8$alkyl, aryl, aryloxy, $C_3$-$C_8$cycloalkyl, $C_3$-$C_8$cycloalkyl $C_1$-$C_8$alkyl, heteroaryl, aryl$C_1$-$C_8$alkyl, heteroaryl$C_1$-$C_8$alkyl, $C_2$-$C_8$alkenyl containing 1 to 2 double bonds, $C_2$-$C_8$alkynyl containing 1 to 2 triple bonds, $C_4$-$C_8$alk(en)(yn)yl groups, cyano, formyl, $C_1$-$C_8$alkylcarbonyl, arylcarbonyl, heteroarylcarbonyl, $C_1$-$C_8$alkoxycarbonyl, aryloxycarbonyl, aminocarbonyl, $C_1$-$C_8$alkylaminocarbonyl, $C_1$-$C_8$dialkylaminocarbonyl, aryl aminocarbonyl, diarylaminocarbonyl, aryl$C_1$-$C_8$alkylaminocarbonyl, halo$C_1$-$C_8$alkoxy, $C_2$-$C_8$alkenyloxy, $C_2$-$C_8$alkynyloxy, aryl$C_1$-$C_8$alkoxy, amino$C_1$-$C_8$alkyl, $C_1$-$C_8$alkylamino$C_1$-$C_8$alkyl, $C_1$-$C_8$dialkylamino$C_1$-$C_8$alkyl, arylamino$C_1$-$C_8$alkyl, amino, $C_1$-$C_8$dialkylamino, arylamino, aryl$C_1$-$C_8$alkylamino, $C_1$-$C_8$alkylcarbonylamino, arylcarbonylamino, azido, mercapto, $C_1$-$C_8$alkylthio, arylthio, halo$C_1$-$C_8$alkylthio, thiocyano, isothiocyano, $C_1$-$C_8$alkylsulfinyl, $C_1$-$C_8$alkylsulfonyl, arylsulfinyl, arylsulfonyl, aminosulfonyl, $C_1$-$C_8$alkylaminosulfonyl, $C_1$-$C_8$dialkylaminosulfonyl and arylaminosulfonyl. When the term "substituted" appears prior to a list of possible substituted groups, it is intended that the term apply to every member of that group.

The term "unsubstituted" refers to a native compound that lacks replacement of an atom or a group of atoms.

DETAILED DESCRIPTION

1. Introduction

Figure 1:
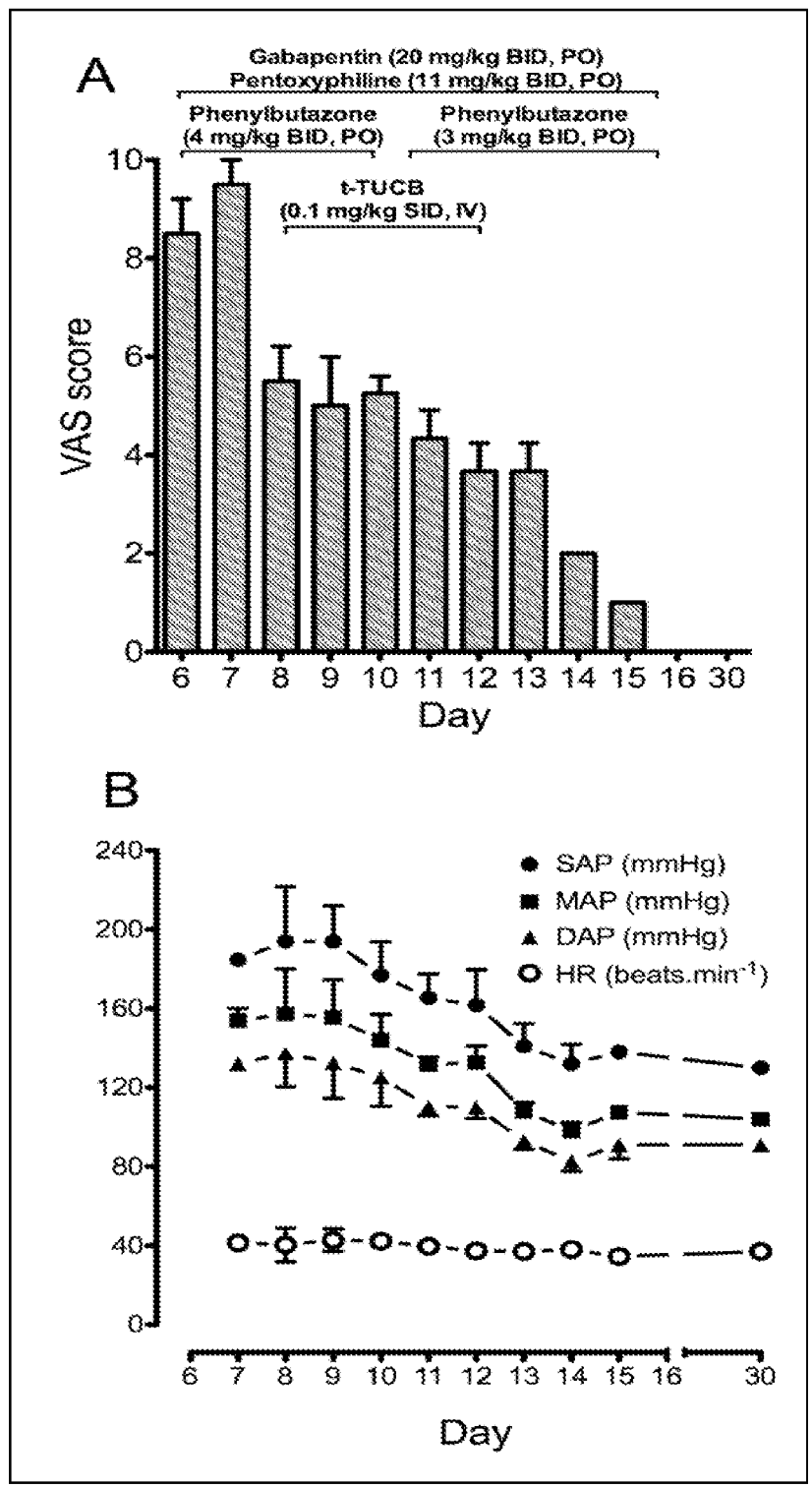
FIG. 1 illustrates daily visual analog pain scores (A), systemic arterial blood pressure and heart rate (B) in one horse with pain due to laminitis, which was treated with multimodal analgesic therapy that included an investigational new drug inhibitor of soluble epoxide hydrolases (t-TUCB). The time frame of drug administration, along with doses, frequency and route of administration is presented above panel A. VAS=visual analog scale (0=no pain, 10=worst pain possible); SAP=systolic arterial pressure; MAP=mean arterial pressure; DAP=diastolic arterial pressure; HR=heart rate. BID=twice daily; SID=once daily; PO=orally; IV=intravenously.

The present invention is based, in part, on the discovery that inhibitors of soluble epoxide hydrolase ("sEH") are efficacious in alleviating, reducing, inhibiting and preventing pain and/or inflammation in non-human mammals, particularly painful and inflammatory conditions that could not be effectively treated using currently employed medications (e.g., non-steroidal anti-inflammatory drugs and/or analgesics were inefficacious), and/or in non-human mammals (e.g., felines, canines) in whom currently employed medications (e.g., non-steroidal anti-inflammatory drugs and/or analgesics) are toxic.

It has been proposed that sEHi-mediated anti-hyperalgesia in inflammatory and neuropathic pain occurs via two distinct mechanisms. One mechanism involves direct anti-inflammatory action of epoxides including down-regulation of induced cyclooxygenase (COX)-2 expression, possibly through a nuclear factor-kappa B (NF-κB)-dependent pathway. Such mechanism mimics the analgesia by non-steroidal anti-inflammatory drugs (NSAIDs) but as transcriptional regulators instead of direct enzyme inhibitors. The second mechanism involves epoxide-mediated up-regulation in steroid/neurosteroid synthesis in the presence of elevated cAMP levels, which then results in analgesia via GABA channels (Inceoglu et al. 2008). Collectively, the multimodal mechanism of action and the favorable interactions with NSAIDs in the ARA cascade suggest that sEH and COX inhibitors combinations may produce significant pain relief while minimizing the risks of NSAID-associated side effects.

The invention finds support in the successful treatment of laminitis in an equine who could not be efficaciously treated using currently available anti-inflammatory and analgesic medications. A 4-year old, 500 kg Thoroughbred female horse diagnosed with bilateral forelimb laminitis and cellulitis on the left forelimb became severely painful and refractory to non-steroidal anti-inflammatory therapy (flunixin meglumine on days 1, 2, 3 and 4; and phenylbutazone on days 5, 6 and 7) alone or in combination with gabapentin (days 6 and 7). Pain scores assessed independently by three individuals with a visual analog scale (VAS; 0=no pain and 10=worst possible pain) were 8.5 on day 6, and it increased to 9.5 on day 7. Non-invasive blood pressure monitoring revealed severe hypertension. As euthanasia was being considered for humane reasons as well as technical and financial constraints, a decision was made to add an experimental new drug, trans-4-{4-[3-(4-Trifluoromethoxy-phenyl)-ureido]-cyclohexyloxy}-benzoic acid (t-TUCB), which is an inhibitor of soluble epoxide hydrolase (sEH), to the treatment protocol. Dose and frequency of administration were selected to produce plasma concentrations within the range of 2.5 μM and 30 nM based on the drug potency against equine sEH. Pain scores decreased sharply and remarkably following t-TUCB administration and blood pressure progressively decreased to physiologic normal values. Plasma concentrations of t-TUCB, measured daily, were within the expected range, whereas phenylbutazone and gabapentin plasma levels were below the suggested efficacious concentrations. No adverse effects were detected on clinical and laboratory examinations during and after t-TUCB administration. The mare did not get any episode of laminitis in the three months following the treatment.

2. Subjects Who May Benefit

The present methods find use in preventing, reducing, inhibiting and/or reversing pain and/or inflammation in a non-human mammal. In various embodiments, the non-human mammal is an ungulate, e.g., equine, bovine, ovine or porcine. In some embodiments, the non-human mammal is canine or feline.

Illustrative non-human mammals who can benefit from the present methods include, e.g., Equidae (e.g., horse, ass, zebra), Bovidae (e.g., cattle, bison, sheep, goat, yak, impala, antelope, hartebeest, wildebeest, gnu, gazelle, water buffalo, duiker), Cervidae (e.g., deer, elk, moose, reindeer, pudu, bororo, brocket, guemal, muntjac), Suidae (e.g., pig, hog, boar), Canidae (domesticated dog, wolf, fox, coyote, jackel), Felidae (e.g., domesticated cat, cheetah, ocelot, lynx, bobcat, mountain lion, leopard, puma, lion, jaguar, tiger), Rodentia (e.g., mouse, rat, guinea pig, chinchilla, agouti, porcupine, beaver, gopher), Lagomorpha (e.g., rabbit, jackrabbit, hare, pika), Camelidae (e.g., camel, llama, alpaca, guanaco, vicugna), Ursidae (e.g., bear, panda), Procyonidae (e.g., raccoon, coati, olingo), Mustelidae (polecat, weasel, ferret, mink, fisher, badger, otter, wolverine, marten, sable, ermine), Elephantidae (e.g., elephant), rhinoceros, hippopotamus and non-human primates (e.g., chimpanzee, bonobo, macaque, ape).

3. Conditions Subject to Prevention and Treatment

In various embodiments, the methods find use in providing relief from pain and/or inflammation in non-human mammals who have received an inefficacious course of treatment for a painful and/or inflamed lesion (e.g., administration of a regime of non-steroidal anti-inflammatory drugs (NSAIDS) or another currently used medication was inefficacious). Inflammatory conditions in non-human animals that can be prevented, reduced, alleviated and/or mitigated by administration of an inhibitor of sEH include without limitation injury or trauma, osteopathic conditions (joint inflammation, panosteitis, osteoarthritis, hip dysplasia), allergic reactions, blockages in the lymphatic system, high blood pressure, heart failure, thyroid disease, liver disease, inflammatory bowel disease, pancreatic inflammation, and chronic kidney disease. The inflammation may be acute or chronic.

In various embodiments, the methods find use in providing relief from pain and/or inflammation for non-human mammals who cannot tolerate therapeutically effective doses of NSAIDS or other active agents other than an inhibitor of sEH for the treatment of pain and/or inflammation (e.g., due to toxicity and/or an inability to metabolize currently available medications). For example, in some embodiments, the non-human mammal received a course of treatment of one or more NSAIDs, as sole active agent or in combination with another active agent other than an inhibitor of sEH, and the course of treatment of one or more NSAIDs did not result in the prevention, reduction, inhibition or reversal of the inflammatory and/or neuropathic pain condition. In some embodiments, an effective regime of one or more NSAIDs cannot be administered to the non-human animal (e.g., would be toxic), and other active agents (that are not a NSAID and are not an inhibitor of sEH) are ineffective in providing the non-human mammal with relief from the painful and/or inflammatory condition. In some embodiments, the non-human mammal has a painful and/or inflammatory condition that could not be effectively prevented, reduced, inhibited and/or reversed by administration of a NSAID co-administered with a Gamma-aminobutyric Acid (GABA) analog (e.g., gabapentin or pregabalin, or analogs or pro-drugs thereof).

In some embodiments, the non-human mammal suffers from tendonitis or arthritis. In some embodiments, the non-human mammal suffers from a chronic inflammatory condition with a neuropathic pain component. Inflammatory pain that has not been treated successfully can evolve into a more chronic pain condition which remains even if the inflammation is resolved. Such chronic or neuropathic pain cannot be effectively reduced, inhibited or reversed by administration of NSAIDS but can be effectively reduced, inhibited or reversed by administration of an inhibitor of sEH as sole active agent, or co-administered with another anti-inflammatory and/or analgesic agent (e.g., a therapeutic or sub-therapeutic amount of an NSAID and/or a Gamma-aminobutyric Acid (GABA) analog (e.g., gabapentin or pregabalin, or analogs or pro-drugs thereof).

In some embodiments, the non-human mammal is an ungulate and suffers from laminitis. Laminitis is a severely debilitating, excruciatingly painful, and life-threatening disease of the soft tissues of the foot of an ungulate, particularly the foot of an equine. Although laminitis has traditionally been viewed as an inflammatory disease, the disorder is far more complex than a simple inflammatory process. The equine foot, complex in both anatomy and physiology, integrates multiple organ systems, including the musculoskeletal, integumentary, nervous, immune, gastrointestinal and cardiovascular systems. Thus, the similarities that are often encountered between animal and human diseases do not occur with equine laminitis. The mode of weight bearing in horses, for example, is fundamentally different from that which occurs in the plantigrade foot. Equines are also unique among ungulates (i.e., cattle, sheep, goats, pigs, etc.) regarding the susceptibility to laminitis. Notwithstanding having structurally similar digit as equines, other ungulates are either not susceptible to laminitis or it occurs to a much lesser degree. Not surprisingly, the precise mechanism underlying laminitic pain remains unclear yet pain control is the single most important task in the clinical management of laminitic horses. Approximately 75% of horses afflicted with laminitis are euthanized due to the seriousness of the disease coupled with lack of efficacious therapies, especially currently available analgesics. Consequently, laminitis is widely considered as one of the most important diseases of horses and a global welfare problem.

Inhibitors of soluble epoxide hydrolase (sEHis), have analgesic and anti-inflammatory effects therapeutically relevant for preventing, reducing, inhibiting and/or reversing equine laminitis. These compounds have been extensively investigated in classic yet simple rodent models of inflammatory and neuropathic pain with very positive results. However, these compounds have not been tested in animals or humans regarding their analgesic effects in naturally occurring diseases. Naturally occurring diseases are typically more complex than animal models, and data obtained in models of disease do not always corroborate with findings in real patients. Here we report the successful use of sEHi for pain management of a horse with naturally occurring laminitis. That sEHi was efficacious in treating pain associated with such a complex disease as laminitis is a remarkable finding. It was more remarkable in that the pain was refractory to therapy with maximum clinically recommended doses of non-steroidal anti-inflammatory drugs and gabapentin. Systematic physical examinations and repeated laboratory analyzes of complete blood cell counts and serum biochemistry revealed no signs of toxicity, demonstrating that sEHis are safe in horses and potentially in other animals. These extraordinary findings represent a notable leap in the field of pain medicine. In this case, we were treating a complex disease involving severe inflammation in a poorly vascularized area and inflammatory pain that likely had evolved into a chronic neuropathic pain condition. The horse was suffering as well from severe hypertension, which could be secondary to the severe pain.

In some embodiments, the non-human mammal suffers from tendonitis or osteoarthritis. Other painful inflammatory diseases such as osteoarthritis (OA) are highly prevalent in domestic animal species (e.g., horses, cats, dogs) and humans. The non-steroidal anti-inflammatory drugs (NSAIDs) are currently the most important class of systemic analgesics to treat OA pain in humans. However, NSAIDs have a relatively narrow safety margin and may have severe toxic side effects when recommended dosages are exceeded and/or prolonged use and/or in susceptible non-human mammals. These adverse effects include gastrointestinal ulceration, renal papillary necrosis, hepatocellular injury, and thrombosis, and are potentially lethal. Among animals, cats are exquisitely sensitive to the toxic effects of NSAIDs. With no approved drugs of this class in the United States for long-term use in cats, management of OA pain in cats is immensely difficult. Inhibitors of sEH have good safety profile in rodents, dogs and non-human primates. Furthermore, no signs of toxicity were detected in a laminitic horse and in preliminary studies in cats. Thus, sEHis find use to fill this gap in the pharmacologic options to treat long-term pain in cats. On the basis of studies in rodent pain models, co-administration of sEHis with low doses of NSAIDs in both horses and dogs with OA pain reduces or minimizes the risks of NSAID-related adverse effects while maintaining analgesic efficacy.

4. Agents that Increase Cis-Epoxyeicosantrienoic Acids ("EETs")

Agents that increase EETs include inhibitors of sEH, EETs, and epoxygenated fatty acids.

a. Inhibitors of sEH

Scores of sEH inhibitors are known, of a variety of chemical structures. Derivatives in which the urea, carbamate or amide pharmacophore are particularly useful as sEH inhibitors. As used herein, "pharmacophore" refers to the section of the structure of a ligand that binds to the sEH. In various embodiments, the urea, carbamate or amide pharmacophore is covalently bound to both an adamantane and to a 12 carbon chain dodecane. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Derivatives of urea are transition state mimetics that form a preferred group of sEH inhibitors. Within this group, N,N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH. Thus, isomers of adamantyl dodecyl urea are preferred inhibitors. It is further expected that N, N'-dodecyl-cyclohexyl urea (DCU), and other inhibitors of sEH, and particularly dodecanoic acid ester derivatives of urea, are suitable for use in the methods. Preferred inhibitors include:

12-(3-Adamantan-1-yl-ureido)dodecanoic acid (AUDA),

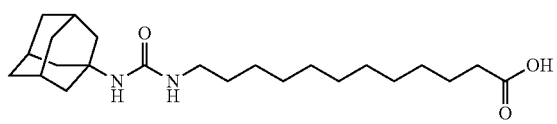 [SMILES: O=C(O)CCCCCCCCCCCNC(=O)NC12CC3CC(CC(C3)C1)C2]

12-(3-Adamantan-1-yl-ureido)dodecanoic acid butyl ester (AUDA-BE),

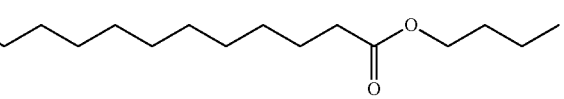

Adamantan-1-yl-3-{5-[2-(2-ethoxyethoxy)ethoxy]pentyl}urea (compound 950, also referred to herein as "AEPU"), and

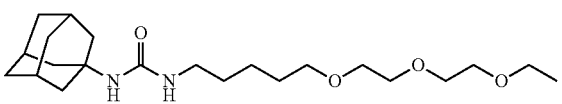 [SMILES: CCOCCOCCOCCCCCNC(=O)NC12CC3CC(CC(C3)C1)C2]

Another preferred group of inhibitors are piperidines. The following Tables sets forth some exemplar inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1

IC$_{50}$ values for selected alkylpiperidine-based sEH inhibitors against human sEH Core structure: 1-adamantyl-NH-C(O)-NH-(CH$_2$)$_n$-(piperidin-4-yl)-N-R

| R: | n = 0 Compound | IC$_{50}$ (μM)[a] | n = 1 Compound | IC$_{50}$ (μM)[a] |
|---|---|---|---|---|
| H | I | 0.30 | II | 4.2 |
| ethyl | 3a | 3.8 | 4a | 3.9 |
| n-butyl | 3b | 0.81 | 4b | 2.6 |
| n-pentyl | 3c | 1.2 | 4c | 0.61 |
| benzyl | 3d | 0.01 | 4d | 0.11 |

[a] As determined via a kinetic fluorescent assay.

TABLE 2 sEH Inhibitor Screen Of Domestic Animals

| Structure | Name | sEHi # | Horse sEH[b] IC$_{50}$ (nM) | Sheep sEH[b] | Pig sEH[a] | Cat sEH[b] | Dog sEH[b] |
|---|---|---|---|---|---|---|---|
| 3-(4-chlorophenyl)-1-(3,4-dichlorophenyl)urea | 3-(4-chlorophenyl)-1-(3,4-dichlorophenyl)urea or 3,4,4'-trichlorocarbanilide | 295 (TCC) | 267 | 56 | 61 | 680 | 5,200 |
| 12-(3-adamantan-1-yl-ureido)dodecanoic acid | 12-(3-adamantan-1-yl-ureido)dodecanoic acid | 700 (AUDA) | 21 | 3 | 11 | 3 | 3 |
| 1-adamantanyl-3-{5-[2-(2-ethoxyethoxy)ethoxy]pentyl}urea | 1-adamantanyl-3-{5-[2-(2-ethoxyethoxy)ethoxy]pentyl}urea | 950 (AEPU) | 23 | 3 | 6 | 27 | 86 |
| 1-(1-acetylpiperidin-4-yl)-3-adamantanylurea | 1-(1-acetylpiperidin-4-yl)-3-adamantanylurea | 1153 (APAU) | 121 | 67 | 13 | 450 | 500 |
| trans-4-[4-(3-Adamantan-1-yl-ureido)-cyclohexyloxy]-benzoic acid | trans-4-[4-(3-Adamantan-1-yl-ureido)-cyclohexyloxy]-benzoic acid | 1471 (tAUCB) | 10 | 5 | 8 | 6 | 1 |

TABLE 2-continued sEH Inhibitor Screen Of Domestic Animals

| Structure | Name | sEHi # | Horse sEH[b] IC$_{50}$ (nM) | Sheep sEH[a] | Pig sEH[a] | Cat sEH[b] | Dog sEH[b] |
|---|---|---|---|---|---|---|---|
| 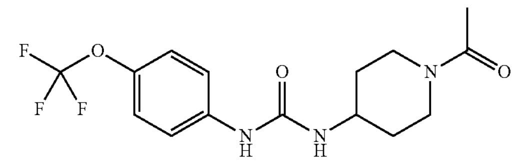 [SMILES: CC(=O)N1CCC(NC(=O)Nc2ccc(OC(F)(F)F)cc2)CC1] | 1-trifluoromethoxy-phenyl-3-(1-acetylpiperidin-4-yl) urea | 1555 (TPAU) | >10,000 | >10,000 | 201 | 480 | 9300 |
| 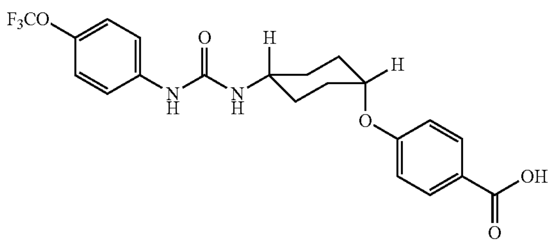 [SMILES: O=C(Nc1ccc(OC(F)(F)F)cc1)NC1CCC(Oc2ccc(C(=O)O)cc2)CC1] | cis-4-[4-(3-Adamantan-1-yl-ureido)-cyclohexyloxy]-benzoic acid | 1686 (cAUCB) | 3 | 1 | 12 | 5 | 4 |
| 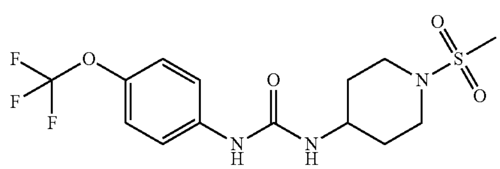 [SMILES: CS(=O)(=O)N1CCC(NC(=O)Nc2ccc(OC(F)(F)F)cc2)CC1] | 1-(1-methylsulfonyl-piperidin-4-yl)-3-(4-trifluoromethoxy-phenyl)-urea | 1709 (TUPS) | 59 | 30 | 60 | 565 | 3200 |
| 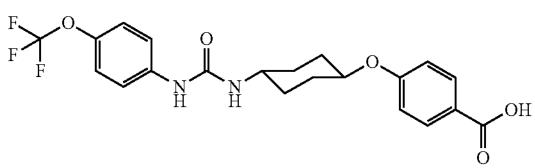 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (tTUCB) | 29 | 6 | | 1 | |
| 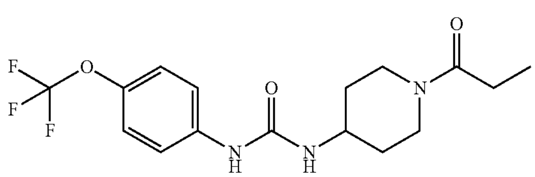 [SMILES: CCC(=O)N1CCC(NC(=O)Nc2ccc(OC(F)(F)F)cc2)CC1] | 1-trifluoromethoxy-phenyl-3-(1-propionylpiperidin-4-yl) urea | 1770 (TPPU) | 68 | 44 | | 400 | |
| 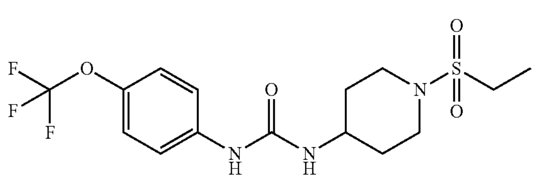 [SMILES: CCS(=O)(=O)N1CCC(NC(=O)Nc2ccc(OC(F)(F)F)cc2)CC1] | 1-(1-ethylsulfonyl-piperidin-4-yl)-3-(4-trifluoromethoxy-phenyl)-urea | 2213 (TUPSE) | 39 | 33 | | | |
| 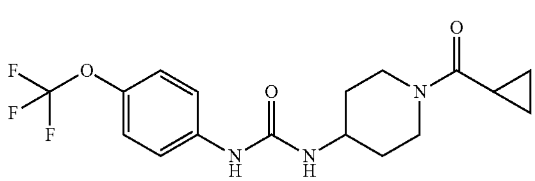 [SMILES: O=C(Nc1ccc(OC(F)(F)F)cc1)NC1CCN(C(=O)C2CC2)CC1] | 1-(1-(cyclo-propanecarbonyl) piperidin-4-yl)-3-(4-(trifluoromethoxy) phenyl)urea | 2214 (CPTU) | 28 | 18 | | 190 | |
| 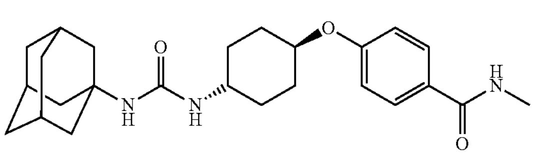 | trans-N-methyl-4-[4-(3-Adamantan-1-yl-ureido)-cyclohexyloxy]-benzamide | 2225 (tMAUCB) | 1 | 1 | | 1 | |

TABLE 2-continued sEH Inhibitor Screen Of Domestic Animals

| Structure | Name | sEHi # | Horse sEH[b] IC$_{50}$ (nM) | Sheep sEH[b] | Pig sEH[a] | Cat sEH[b] | Dog sEH[b] |
|---|---|---|---|---|---|---|---|
| 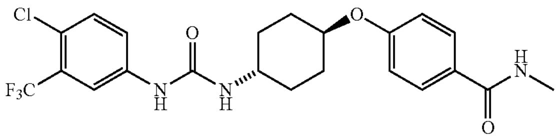 | trans-N-methyl-4-[4-((3-trifluoromethyl-4-chlorophenyl)-ureido)-cyclohexyloxy]-benzamide | 2226 (tMTCUCB) | 1 | 1 | | | 4 |
| 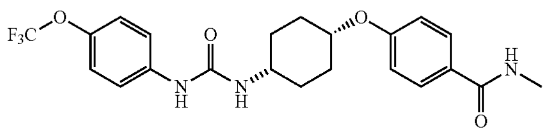 | cis-N-methyl-4-{4-[3-(4-trifluoromethoxy-phenyl)-ureido]-cyclohexyloxy}-benzamide | 2228 (cMTUCB) | 1 | 1 | | | 2 |
| 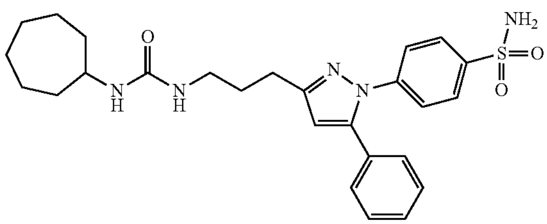 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propyl)urea | 2247 (HDP3U) | 1 | 2 | | | |

[a]measured with MNPC on recombinant enzyme.
[b]measured with radioactive assay and liver cytosolic preparation.

TABLE 3 sEH Inhibitor Screen of Canine sEH

| Structure | Name | sEHI# | Inhibition % for [I] = 100 nM | IC$_{50}$ (nM) |
|---|---|---|---|---|
| 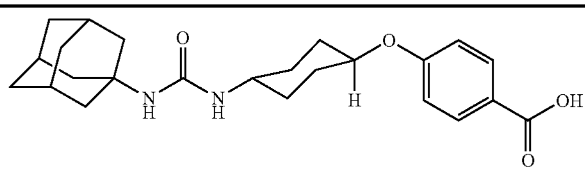 | trans-4-[4-(3-Adamantan-1-yl-ureido)-cyclohexyloxy]-benzoic acid | 1471 | 97 | <1 |
| 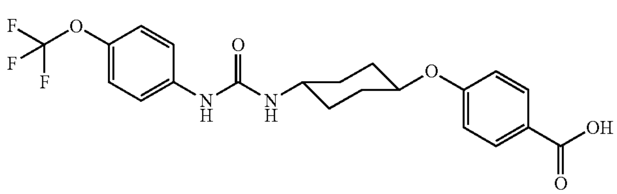 [SMILES: O=C(Nc1ccc(OC(F)(F)F)cc1)NC1CCC(Oc2ccc(C(=O)O)cc2)CC1] | 4-{4-[3-(4-Trifluoromethoxy-phenyl)-ureido]-cyclohexyloxy}-benzoic acid | 1728 | 92 | 14 |
| 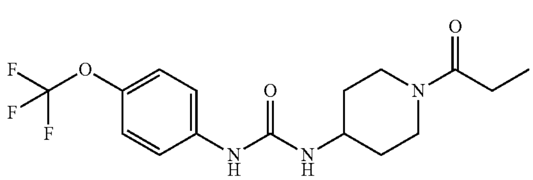 [SMILES: CCC(=O)N1CCC(NC(=O)Nc2ccc(OC(F)(F)F)cc2)CC1] | 1-trifluoromethoxyphenyl-3-(1-propionylpiperidin-4-yl) urea | 1770 | 58 | |
| 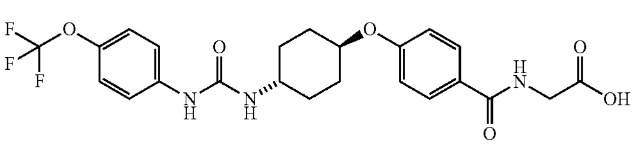 | trans-2-(4-(4-(3-(4-trifluoromethoxy-phenyl)-ureido)-cyclohexyloxy)-benzamido)-acetic acid | 2283 | 64 | |

TABLE 3-continued sEH Inhibitor Screen of Canine sEH

| Structure | Name | sEHI# | Inhibition % for [I] = 100 nM | IC$_{50}$ (nM) |
|---|---|---|---|---|
| 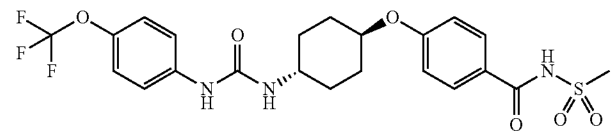 [SMILES: CS(=O)(=O)NC(=O)c1ccc(O[C@H]2CC[C@H](NC(=O)Nc3ccc(OC(F)(F)F)cc3)CC2)cc1] | N-(methylsulfonyl)-4-(trans-4-(3-(4-trifluoromethoxy-phenyl)-ureido)-cyclohexyloxy)-benzamide | 2728 | 84 | 100 |
| 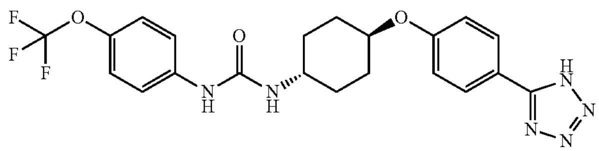 [SMILES: O=C(Nc1ccc(OC(F)(F)F)cc1)N[C@H]1CC[C@H](Oc2ccc(-c3nnn[nH]3)cc2)CC1] | 1-(trans-4-(4-(1H-tetrazol-5-yl)-phenoxy)-cyclohexyl)-3-(4-(trifluoromethoxy)-phenyl)-urea | 2806 | 99 | <1 |
| 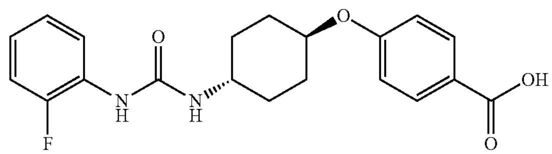 [SMILES: O=C(Nc1ccccc1F)N[C@H]1CC[C@H](Oc2ccc(C(=O)O)cc2)CC1] | 4-(trans-4-(3-(2-fluorophenyl)-ureido)-cyclohexyloxy)-benzoic acid | 2736 | 80 | 39 |
| 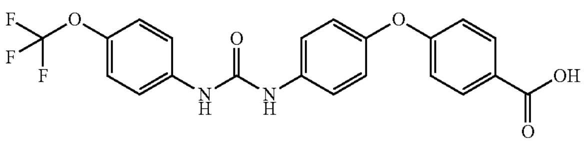 [SMILES: O=C(Nc1ccc(Oc2ccc(C(=O)O)cc2)cc1)Nc1ccc(OC(F)(F)F)cc1] | 4-(4-(3-(4-(trifluoromethoxy)-phenyl)-ureido)-phenoxy)-benzoic acid | 2803 | 82 | 42 |
| 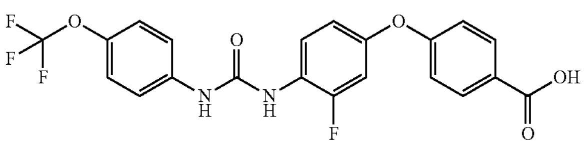 [SMILES: O=C(Nc1ccc(OC(F)(F)F)cc1)Nc1ccc(Oc2ccc(C(=O)O)cc2)cc1F] | 4-(3-fluoro-4-(3-(4-(trifluoromethoxy)-phenyl)-ureido)-phenoxy)-benzoic acid | 2807 | 95 | 14 |
| 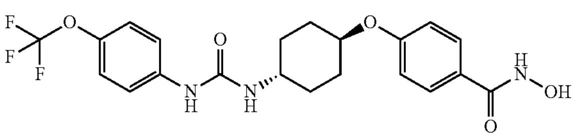 [SMILES: O=C(Nc1ccc(OC(F)(F)F)cc1)N[C@H]1CC[C@H](Oc2ccc(C(=O)NO)cc2)CC1] | N-hydroxy-4-(trans-4-(3-(4-(trifluoromethoxy)-phenyl)-ureido)-cyclohexyloxy)-benzamide | 2761 | 72 | |
| 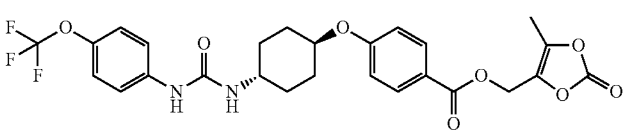 [SMILES: Cc1oc(=O)oc1COC(=O)c1ccc(O[C@H]2CC[C@H](NC(=O)Nc3ccc(OC(F)(F)F)cc3)CC2)cc1] | (5-methyl-2-oxo-1,3-dioxol-4-yl)methyl 4-((1r,4r)-4-(3-(4-(trifluoromethoxy)-phenyl)-ureido)-cyclohexyloxy)-benzoate | 2796 | 84 | 38 |
| 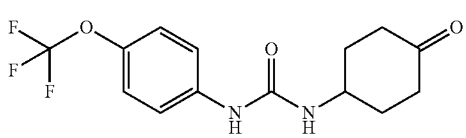 [SMILES: O=C1CCC(NC(=O)Nc2ccc(OC(F)(F)F)cc2)CC1] | 1-(4-oxocyclohexyl)-3-(4-(trifluoromethoxy)-phenyl)-urea | 2809 | 51 | |
| 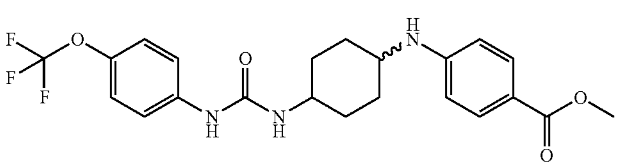 [SMILES: COC(=O)c1ccc(NC2CCC(NC(=O)Nc3ccc(OC(F)(F)F)cc3)CC2)cc1] | methyl 4-(4-(3-(4-(trifluoromethoxy)-phenyl)-ureido)-cyclohexylamino)-benzoate | 2804 | 49 | |
| 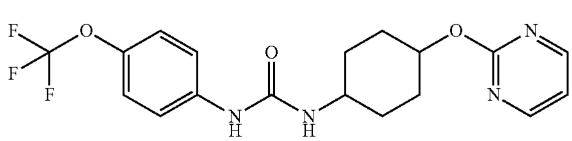 [SMILES: O=C(Nc1ccc(OC(F)(F)F)cc1)NC1CCC(Oc2ncccn2)CC1] | 1-(4-(pyrimidin-2-yloxy)-cyclohexyl)-3-(4-(trifluoromethoxy)-phenyl)-urea | 2810 | 52 | |

TABLE 3-continued sEH Inhibitor Screen of Canine sEH

| Structure | Name | sEHI# | Inhibition % for [I] = 100 nM | IC$_{50}$ (nM) |
|---|---|---|---|---|
| 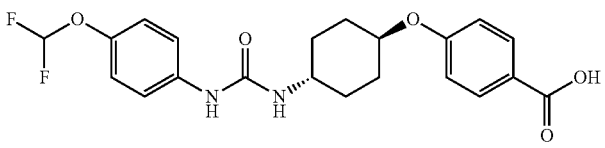 [SMILES: O=C(Nc1ccc(OC(F)F)cc1)N[C@H]1CC[C@H](Oc2ccc(C(=O)O)cc2)CC1] | 4-(trans-4-(3-(4-(difluoromethoxy)-phenyl)-ureido)-cyclohexyloxy)-benzoic acid | 2805 | 95 | 19 |

A number of other sEH inhibitors which can be used in the methods and compositions are set forth in co-owned applications PCT/US2012/025074, PCT/US2011/064474, PCT/US2011/022901, PCT/US2008/072199, PCT/US2007/006412, PCT/US2005/038282, PCT/US2005/08765, PCT/US2004/010298 and U.S. Published Patent Application Publication 2005/0026844, each of which is hereby incorporated herein by reference in its entirety for all purposes.

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S,S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. No. 6,150,415 (the '415 patent) and U.S. Pat. No. 6,531,506 (the '506 patent). Two preferred classes of sEH inhibitors are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty sEH inhibitors of Formula 2, which were shown to inhibit human sEH at concentrations as low as 0.1 µM. Any particular sEH inhibitor can readily be tested to determine whether it will work in the methods by standard assays. Esters and salts of the various compounds discussed above or in the cited patents, for example, can be readily tested by these assays for their use in the methods.

As noted above, chalcone oxides can serve as an alternate substrate for the enzyme. While chalcone oxides have half-lives which depend in part on the particular structure, as a group the chalcone oxides tend to have relatively short half-lives (a drug's half-life is usually defined as the time for the concentration of the drug to drop to half its original value. See, e.g., Thomas, G., Medicinal Chemistry: an introduction, John Wiley & Sons Ltd. (West Sussex, England, 2000)). Since the various uses contemplate inhibition of sEH over differing periods of time which can be measured in days, weeks, or months, chalcone oxides, and other inhibitors which have a half-life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half-lives although, for inhibitors with a relatively short half-life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as pro-drugs or protoxins (Gilman et al., The Pharmacological Basis of Therapeutics, 7th Edition, MacMillan Publishing Company, New York, p. 16 (1985)) Esters, for example, are common pro-drugs which are released to give the corresponding alcohols and acids enzymatically (Yoshigae et al., Chirality, 9:661-666 (1997)). The drugs and pro-drugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many pro-drugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHi, however, may diffuse or be transported following administration to regions where their activity in inhibiting sEH may not be desired. Thus, multiple soft drugs for treatment have been prepared. These include but are not limited to carbamates, esters, carbonates and amides placed in the sEHi, approximately 7.5 angstroms from the carbonyl of the central pharmacophore. These are highly active sEHi that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, a compound with combined functionality to concurrently inhibit sEH and COX-2 is administered. Urea-containing pyrazoles that function as dual inhibitors of cyclooxygenase-2 and soluble epoxide hydrolase are described, e.g., in Hwang, et al., *J Med Chem.* (2011) 28; 54(8):3037-50.

Preferably, the inhibitor inhibits sEH without also significantly inhibiting microsomal epoxide hydrolase ("mEH"). Preferably, at concentrations of 100 µM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 100 µM. Inhibitors with $IC_{50}$s of less than 100 µM are preferred, with $IC_{50}$s of less than 75 µM being more preferred, and, in order of increasing preference, an $IC_{50}$ of 50 µM, 40 µM, 30 µM, 25 µM, 20 µM, 15 µM, 10 µM, 5 µM, 3 µM, 2 µM, 1 µM, 100 nM, 10 nM, 1.0 nM, or even less, being still more preferred. Assays for determining sEH activity are known in the art and described elsewhere herein.

The $IC_{50}$ determination of the inhibitor can be made with respect to an sEH enzyme from the species subject to treatment (e.g., the subject receiving the inhibitor of sEH).

b. Cis-Epoxyeicosantrienoic Acids ("EETs")

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. For example, in one prior report of EETs administration, EETs were administered by catheters inserted into mouse aortas. The EETs were infused continuously during the course of the experiment because of concerns over the short half-life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

Studies from the laboratory of the present inventors, however, showed that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be administered without also administering an sEHi to provide a therapeutic effect. Moreover, EETs, if not exposed to acidic conditions or to sEH are stable and can withstand reasonable storage, handling and administration.

In short, sEHi, EETs, or co-administration of sEHis and of EETs, can be used in the methods of the present invention. In some embodiments, one or more EETs are administered to the patient without also administering an sEHi. In some embodiments, one or more EETs are administered shortly before or concurrently with administration of an sEH inhibitor to slow hydrolysis of the EET or EETs. In some embodiments, one or more EETs are administered after administration of an sEH inhibitor, but before the level of the sEHi has diminished below a level effective to slow the hydrolysis of the EETs.

EETs useful in the methods of the present invention include 14,15-EET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

If desired, EETs, analogs, or derivatives that retain activity can be used in place of or in combination with unmodified EETs. Liao and Zeldin, supra, define EET analogs as compounds with structural substitutions or alterations in an EET, and include structural analogs in which one or more EET olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, urea, amide, carbamate, difluorocycloprane, or carbonyl, while in others, the carboxylic acid moiety is stabilized by blocking beta oxidation or is replaced with a commonly used mimic, such as a nitrogen heterocycle, a sulfonamide, or another polar functionality. In preferred forms, the analogs or derivatives are relatively stable as compared to an unmodified EET because they are more resistant than an unmodified EET to sEH and to chemical breakdown. "Relatively stable" means the rate of hydrolysis by sEH is at least 25% less than the hydrolysis of the unmodified EET in a hydrolysis assay, and more preferably 50% or more lower than the rate of hydrolysis of an unmodified EET. Liao and Zeldin show, for example, episulfide and sulfonamide EETs derivatives. Amide and ester derivatives of EETs and that are relatively stable are preferred embodiments. Whether or not a particular EET analog or derivative has the biological activity of the unmodified EET can be readily determined by using it in standard assays, such as radio-ligand competition assays to measure binding to the relevant receptor. As mentioned in the Definition section, above, for convenience of reference, the term "EETs" as used herein refers to unmodified EETs, and EETs analogs and derivatives unless otherwise required by context.

In some embodiments, the EET or EETs are embedded or otherwise placed in a material that releases the EET over time. Materials suitable for promoting the slow release of compositions such as EETs are known in the art. Optionally, one or more sEH inhibitors may also be placed in the slow release material.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice.

c. Assays for Epoxide Hydrolase Activity

Any of a number of standard assays for determining epoxide hydrolase activity can be used to determine inhibition of sEH. For example, suitable assays are described in Gill, et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

d. Other Means of Inhibiting sEH Activity

Other means of inhibiting sEH activity or gene expression can also be used in the methods herein. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, siRNA were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). An exemplary amino acid sequence of human sEH (GenBank Accession No. L05779; SEQ ID NO:1) and an exemplary nucleotide sequence encoding that amino acid sequence (GenBank Accession No. AAA02756; SEQ ID NO:2) are set forth in U.S. Pat. No. 5,445,956. The nucleic acid sequence of human sEH is also published as GenBank Accession No. NM_001979.4; the amino acid sequence of human sEH is also published as GenBank Accession No. NP_001970.2.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

For example, using the program available from the Whitehead Institute, the following sEH target sequences and siRNA sequences can be generated:

```
1) Target:
                                    (SEQ ID NO: 3)
CAGTGTTCATTGGCCATGACTGG Sense-siRNA:
                                    (SEQ ID NO: 4)
5' - GUGUUCAUUGGCCAUGACUTT - 3'

Antisense-siRNA:
                                    (SEQ ID NO: 5)
5' - AGUCAUGGCCAAUGAACACTT - 3'
```

```
2) Target:
                                    (SEQ ID NO: 6)
GAAAGGCTATGGAGAGTCATCTG Sense-siRNA:
                                    (SEQ ID NO: 7)
5' - AAGGCUAUGGAGAGUCAUCTT - 3'

Antisense-siRNA:
                                    (SEQ ID NO: 8)
5'- GAUGACUCUCCAUAGCCUUTT - 3'

3) Target
                                    (SEQ ID NO: 9)
AAAGGCTATGGAGAGTCATCTGC Sense-siRNA:
                                    (SEQ ID NO: 10)
5' - AGGCUAUGGAGAGUCAUCUTT- 3'

Antisense-siRNA:
                                    (SEQ ID NO: 11)
5' - AGAUGACUCUCCAUAGCCUTT- 3'

4) Target:
                                    (SEQ ID NO: 12)
CAAGCAGTGTTCATTGGCCATGA Sense-siRNA:
                                    (SEQ ID NO: 13)
5' - AGCAGUGUUCAUUGGCCAUTT- 3'

Antisense-siRNA:
                                    (SEQ ID NO: 14)
5' - AUGGCCAAUGAACACUGCUTT- 3'

5) Target:
                                    (SEQ ID NO: 15)
CAGCACATGGAGGACTGGATTCC Sense-siRNA:
                                    (SEQ ID NO: 16)
5' - GCACAUGGAGGACUGGAUUTT- 3'

Antisense-siRNA:
                                    (SEQ ID NO: 17)
5' - AAUCCAGUCCUCCAUGUGCTT- 3'
```

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 by siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 by dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

1) Target:
(SEQ ID NO: 19)
CAGTGTTCATTGGCCATGACTGG

Sense strand:
(SEQ ID NO: 20)
5'-GATCCCCGTGTTCATTGGCCATGACTTTCAA

GAGAAGTCATGGCCAATGAACACTTTTT-3'

Antisense strand:
(SEQ ID NO: 21)
5'-AGCTAAAAAGTGTTCATTGGCCATGACTTCTCTT

GAAAGTCATGGCCAATGAACACGGG -3'

2) Target:
(SEQ ID NO: 22)
GAAAGGCTATGGAGAGTCATCTG

Sense strand:
(SEQ ID NO: 23)
5'-GATCCCCAAGGCTATGGAGAGTCATCTTCAAGAGAGA

TGACTCTCCATAGCCTTTTTT -3'

Antisense strand:
(SEQ ID NO: 24)
5'- AGCTAAAAAAAGGCTATGGAGAGTCATCTCTCTTGAA

GATGACTCTCCATAGCCTTGGG -3'

3) Target:
(SEQ ID NO: 25)
AAAGGCTATGGAGAGTCATCTGC

Sense strand:
(SEQ ID NO: 26)
5'-GATCCCCAGGCTATGGAGAGTCATCTTTCAAGAGAAG

ATGACTCTCCATAGCCTTTTTT -3'

Antisense strand:
(SEQ ID NO: 27)
5'-AGCTAAAAAAGGCTATGGAGAGTCATCATCTCTTGAAAGATGACTCT

CCATAGCCTGGG -3'

4) Target:
(SEQ ID NO: 28)
CAAGCAGTGTTCATTGGCCATGA

Sense strand:
(SEQ ID NO: 29)
5'-GATCCCCAGCAGTGTTCATTGGCCATTTCAAGAGAATG

GCCAATGAACACTGCTTTTTT -3'

Antisense strand:
(SEQ ID NO: 30)
5'- AGCTAAAAAAGCAGTGTTCATTGGCCATTCTCTTGAAATG

GCCAATGAACACTGCTGGG -3'

5) Target:
(SEQ ID NO: 31)
CAGCACATGGAGGACTGGATTCC

Sense strand
(SEQ ID NO: 32)
5'-GATCCCCGCACATGGAGGACTGGATTTTCAAGAGAAATC

CAGTCCTCCATGTGCTTTTT -3'

Antisense strand:
(SEQ ID NO: 33)
5'- AGCTAAAAAGCACATGGAGGACTGGATTTCTCTTGAAAA

TCCAGTCCTCCATGTGCGGG -3'

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264:17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program found on the worldwide web "biotools.idtdna.com/antisense/AntiSense.aspx", which will provide appropriate antisense sequences for nucleic acid sequences up to 10,000 nucleotides in length. Using this program with the sEH gene provides the following exemplar sequences:

```
                                    (SEQ ID NO: 34)
1) UGUCCAGUGCCCACAGUCCU (SEQ ID NO: 35)
2) UUCCCACCUGACACGACUCU (SEQ ID NO: 36)
3) GUUCAGCCUCAGCCACUCCU (SEQ ID NO: 37)
4) AGUCCUCCCGCUUCACAGA (SEQ ID NO: 38)
5) GCCCACUUCCAGUUCCUUUCC
```

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate ligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found on the worldwide web at "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11): 4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol Chem. 279(40):42230-9 (2004); Ying and Lin, Biochem Biophys Res Commun. 326(3):515-20 (2005).

5. Epoxygenated Fatty Acids

In some embodiments, an epoxygenated fatty acid is administered as an agent that increases EETs. Illustrative epoxygenated fatty acids include epoxides of linoleic acid, eicosapentaenoic acid ("EPA") and docosahexaenoic acid ("DHA").

The fatty acids eicosapentaenoic acid ("EPA") and docosahexaenoic acid ("DHA") have recently become recognized as having beneficial effects, and fish oil tablets, which are a good source of these fatty acids, are widely sold as supplements. In 2003, it was reported that these fatty acids reduced pain and inflammation. Sethi, S. et al., Blood 100:

1340-1346 (2002). The paper did not identify the mechanism of action, nor the agents responsible for this relief.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

As mentioned, it is beneficial to elevate the levels of EETs, which are epoxides of the fatty acid arachidonic acid. Our studies of the effects of EETs has led us to realization that the anti-inflammatory effect of EPA and DHA are likely due to increasing the levels of the epoxides of these two fatty acids. Thus, increasing the levels of epoxides of EPA, of DHA, or of both, will act to reduce pain and inflammation, and symptoms associated with diabetes and metabolic syndromes, in mammals in need thereof. This beneficial effect of the epoxides of these fatty acids has not been previously recognized. Moreover, these epoxides have not previously been administered as agents, in part because, as noted above, epoxides have generally been considered too labile to be administered.

Like EETs, the epoxides of EPA and DHA are substrates for sEH. The epoxides of EPA and DHA are produced in the body at low levels by the action of cytochrome P450s. Endogenous levels of these epoxides can be maintained or increased by the administration of sEHi. However, the endogenous production of these epoxides is low and usually occurs in relatively special circumstances, such as the resolution of inflammation. Our expectation is that administering these epoxides from exogenous sources will aid in the resolution of inflammation and in reducing pain, as well as with symptoms of diabetes and metabolic syndromes. It is further beneficial with pain or inflammation to inhibit sEH with sEHi to reduce hydrolysis of these epoxides, thereby maintaining them at relatively high levels.

EPA has five unsaturated bonds, and thus five positions at which epoxides can be formed, while DHA has six. The epoxides of EPA are typically abbreviated and referred to generically as "EpETEs", while the epoxides of DHA are typically abbreviated and referred to generically as "EpDPEs". The specific regioisomers of the epoxides of each fatty acid are set forth in the following Table:

TABLE A

Regioisomers of Eicosapentaenoic acid ("EPA") epoxides:

1. Formal name: (±)5(6)-epoxy-8Z, 11Z, 14Z, 17Z-eicosatetraenoic acid,
Synonym 5(6)-epoxy Eicosatetraenoic acid
Abbreviation 5(6)-EpETE
2. Formal name: (±)8(9)-epoxy-5Z, 11Z, 14Z, 17Z -eicosatetraenoic acid,
Synonym 8(9)-epoxy Eicosatetraenoic acid
Abbreviation 8(9)-EpETE
3. Formal name: (±)11(12)-epoxy-5Z, 8Z, 14Z, 17Z -eicosatetraenoic acid,
Synonym 11(12)-epoxy Eicosatetraenoic acid
Abbreviation 11(12)-EpETE TABLE A-continued 4. Formal name: (±)14(15)-epoxy-5Z, 8Z, 11Z, 17Z-eicosatetraenoic acid,
Synonym 14(15)-epoxy Eicosatetraenoic acid
Abbreviation 14(15)-EpETE
5. Formal name: (±)17(18)-epoxy-5Z, 8Z, 11Z, 14Z-eicosatetraenoic acid,
Synonym 17(18)-epoxy Eicosatetraenoic acid
Abbreviation 17(18)-EpETE Regioisomers of Docosahexaenoic acid ("DHA") epoxides:

1. Formal name: (±) 4(5)-epoxy-7Z, 10Z, 13Z, 16Z, 19Z -docosapentaenoic acid,
Synonym 4(5)-epoxy Docosapentaenoic acid
Abbreviation 4(5)-EpDPE
2. Formal name: (±) 7(8)-epoxy-4Z, 10Z, 13Z, 16Z, 19Z -docosapentaenoic acid,
Synonym 7(8)-epoxy Docosapentaenoic acid
Abbreviation 7(8)-EpDPE
3. Formal name: (±)10(11)-epoxy-4Z, 7Z, 13Z, 16Z, 19Z -docosapentaenoic acid,
Synonym 10(11)-epoxy Docosapentaenoic acid
Abbreviation 10(11)-EpDPE
4. Formal name: (±)13(14)-epoxy-4Z, 7Z, 10Z, 16Z, 19Z -docosapentaenoic acid,
Synonym 13(14)-epoxy Docosapentaenoic acid
Abbreviation 13(14)-EpDPE
5. Formal name: (±) 16(17)-epoxy-4Z, 7Z, 10Z, 13Z, 19Z -docosapentaenoic acid,
Synonym 16(17)-epoxy Docosapentaenoic acid
Abbreviation 16(17)-EpDPE
6. Formal name: (±) 19(20)-epoxy-4Z, 7Z, 10Z, 13Z, 16Z -docosapentaenoic acid,
Synonym 19(20)-epoxy Docosapentaenoic acid
Abbreviation 19(20)-EpDPE Any of these epoxides, or combinations of any of these, can be administered in the compositions and methods.

6. Co-Administration with Anti-Inflammatory and/or Analgesic Agents

In various embodiments, the agent that increases EETs (e g., inhibitor of sEH, EET, epoxygenated fatty acid, and mixtures thereof) is co-administered with an anti-inflammatory and/or analgesic agent. One or both of the agent that increases EETs and the anti-inflammatory and/or analgesic agent can be administered in a sub-therapeutic amount.

a. Inhibitors of COX-1 and/or COX-2

Current non-steroidal anti-inflammatory drugs (NSAIDs) inhibit both isoforms, but most tend to inhibit the two isoforms to different degrees. Since COX-2 is considered the enzyme associated with an inflammatory response, enzyme selectivity is generally measured in terms of specificity for COX-2. Typically, cells of a target organ that express COX-1 or COX-2 are exposed to increasing levels of NSAIDs. If the cell does not normally produce COX-2, COX-2 is induced by a stimulant, usually bacterial lipopolysaccharide (LPS).

The relative activity of NSAIDs on COX-1 and COX-2 is expressed by the ratio of $IC_{50}$s for each enzyme: COX-2 ($IC_{50}$)/COX-1 ($IC_{50}$). The smaller the ratio, the more specific the NSAID is for COX-2. For example, various NSAIDs have been reported to have ratios of COX-2 ($IC_{50}$)/COX-1 ($IC_{50}$) ranging from 0.33 to 122. See, Englehart et al., J Inflammatory Res 44:422-33 (1995). Aspirin has an $IC_{50}$ ratio of 0.32, indicating that it inhibits COX-1 more than COX-2, while indomethacin is considered a COX-2 inhibitor since its COX-2 ($IC_{50}$)/COX-1 ($IC_{50}$) ratio is 33. Even selective COX-2 inhibitors retain some COX-1 inhibition at therapeutic levels obtained in vivo. Cryer and Feldman, Am J Med. 104(5):413-21 (1998).

Commercially available NSAIDs that find use in the methods and compositions include the traditional NSAIDs diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, the selective COX-2 inhibitors celecoxib, rofecoxib, and valdecoxib, the acetylated salicylates, such as aspirin, and the non-acetylated salicylates, such as magnesium salicylate, choline salicylate, salsalate, salicylic acid esters and sodium salicylate.

b. Inhibitors of 5-LOX

Metabolism of arachidonic acid through the lipoxygenase ("LOX") pathway lead to the formation of leukotrienes ("LTs") that are implicated in a range of pathologies. The primary inflammatory enzyme is 5-lipoxygenase ("5-LOX"). The 5-LOX cascade results in the formation of LTB4 and the cysteinyl LTs LTC4, LTD4, and LTE4. LTB4 is a potent stimulator of leukocyte activation. Cysteinyl LTs "may participate in the damage of gastric mucosa by inducing mucosal microvascular injury and gastric vessel vasoconstriction, promoting breakdown of the mucosal barrier and stimulating the secretion of gastric acid, as well as the production of interleukin 1 ("IL1") and proinflammatory cytokines." Martel-Pelletier et al., Ann. Rheumatic Dis 62:501-509 (2003) ("Martel-Pelletier 2003"). Additional lipoxygenases, 12-LOX and 15-LOX, exist that contribute to the formation of anti-inflammatory compounds known as lipoxins, or LXs. Thus, for purposes of reducing inflammation, it is desirable to inhibit 5-LOX without also inhibiting 12-LOX and 15-LOX.

Because of its role in inflammation, a number of inhibitors of 5-LOX have been developed. See, e.g., Julemont et al., Expert Opinion on Therapeutic Patents, 13(1):1-13 (2003) (review of patents directed to 5-LOX inhibitors for 1999-2002). One orally effective inhibitor is REV 5901 [alpha-pentyl-3-(2-quinolinylmethoxy)-benzene-methanol] (see, Van Inwegen et al., Pharmacol Exp Therapeutics 241(1): 117-124 (1987)). 5-LOX can also be inhibited by inhibiting the 5-lipoxygenase activating protein ("FLAP") by MK-886. (see, Smirnov et al., Br J Pharmacol 124:572-578 (1998)). This inhibitor, however, induces apoptosis in some cell types and is best used in in vitro studies. Other inhibitors are described in, e.g., U.S. Patent Application No. 20040198768 c. Joint COX/LOX Inhibitors

Because of the inflammatory effects of prostaglandins and leukotrienes, and because blocking the COX pathway has been thought to shuttle arachidonic acid into the LOX pathway, it has been suggested that dual inhibition of both COX-2 and 5-LOX would maximize the inhibition of inflammation. See, e.g., Martel-Pelletier 2003, supra. Several compounds have been developed to block both COX-2 and 5-LOX. One, tepoxalin, blocks COX-1, COX-2, and 5-LOX, and is commercially available as a veterinary pharmaceutical for dogs, under the name Zubrin® (Schering Plough Animal Health Corp., Union, N.J.). Tepoxalin has also been shown to block the COX enzymes and LOX in humans and to be well tolerated. A second inhibitor of COX and 5-LOX, licofelone (Merkle GmbH, Germany), is in Phase III clinical trials as a treatment for osteoarthritis and has shown gastric tolerability superior to naproxen. See, Bias et al., Am J Gastroenterol 99(4):611 (2004). See also, Martel-Pelletier 2003, supra; Tries et al., Inflamm Res 51:135-43 (2002). A number of other dual COX/LOX inhibitors, and especially COX-2/5-LOX inhibitors, have been developed, as exemplified by U.S. Pat. No. 6,753,344 (thiophene substituted hydroxamic acid derivatives), U.S. Pat. No. 6,696,477 (heterocyclo substituted hydroxamic acid derivatives), U.S. Pat. No. 6,677,364 (substituted sulfonylphenylheterocycles), and U.S. Patent Application Nos. 20040248943 (pyrazole substituted hydroxamic acid derivatives), 20040147565 (substituted sulfonylphenylheterocycles), 20030180402 (flavans isolated from the genus *Acacia*), and 20030176708 (thiophene substituted hydroxamic acid derivatives).

d. Phosphodiesterase Inhibitors (PDEi)

In various embodiments, the inhibitor of sEH is co-administered with an inhibitor of phosphodiesterase. The PDEi may or may not be selective, specific or preferential for cAMP. Exemplary PDEs that degrade cAMP include without limitation PDE3, PDE4, PDE7, PDE8 and PDE10. Exemplary cAMP selective hydrolases include PDE4, 7 and 8. Exemplary PDEs that hydrolyse both cAMP and cGMP include PDE1, 2, 3, 10 and 11. Isoenzymes and isoforms of PDEs are well known in the art. See, e.g., Boswell-Smith et al., *Brit. J. Pharmacol.* 147:S252-257 (2006), and Reneerkens, et al., *Psychopharmacology* (2009) 202:419-443, the contents of which are incorporated herein by reference.

In some embodiments, the PDE inhibitor is a non-selective inhibitor of PDE. Exemplary non-selective PDE inhibitors that find use include without limitation caffeine, theophylline, isobutylmethylxanthine, aminophylline, pentoxifylline, vasoactive intestinal peptide (VIP), secretin, adrenocorticotropic hormone, pilocarpine, alpha-melanocyte stimulating hormone (MSH), beta-MSH, gamma-MSH, the ionophore A23187, prostaglandin E1.

In some embodiments, the PDE inhibitor used specifically or preferentially inhibits PDE4. Exemplary inhibitors that selectively inhibit PDE4 include without limitation rolipram, roflumilast, cilomilast, ariflo, HT0712, ibudilast and mesembrine.

In some embodiments, the PDE inhibitor used specifically or preferentially inhibits a cAMP PDE, e.g., PDE4, PDE7 or PDE8. In some embodiments, the PDE inhibitor used inhibits a cAMP PDE, e.g., PDE1, PDE2, PDE3, PDE4, PDE7, PDE8, PDE10 or PDE11. Exemplary agents that inhibit a cAMP phosphodiesterase include without limitation rolipram, roflumilast, cilomilast, ariflo, HT0712, ibudilast, mesembrine, cilostamide, enoxamone, milrinone, siguazodan and BRL-50481.

In some embodiments, the PDE inhibitor used specifically inhibits PDE5. Exemplary inhibitors that selectively inhibit PDE5 include without limitation sildenafil, zaprinast, tadalafil, udenafil, avanafil and vardenafil.

Other means of inhibiting phosphodiesterase activity or gene expression can also be used in the methods described herein. For example, a nucleic acid molecule complementary to at least a portion of a human phosphodiesterase gene (e.g., PDE3, PDE4, PDE7, PDE8 and PDE10) can be used to inhibit phosphodiesterase gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., *Science,* 305(5688):1289-92 (2004); He and Hannon, *Nat Rev Genet.* 5(7):522-31 (2004).

For purposes of reducing the activity of a phosphodiesterase enzyme, siRNAs to the gene encoding the phosphodiesterase can be specifically designed using computer programs. Exemplary nucleotide sequences encoding the amino acid sequences of the various phosphodiesterase isoforms are known and published, e.g., in GenBank, e.g., PDE1A (NM_001003683.1→NP_001003683.1 (isoform 2) and NM_005019.3→NP_005010.2 (isoform 1)); PDE1B (NM_000924.3→NP_000915.1 (isoform 1) and NM_001165975.1→NP_001159447.1 (isoform 2)); PDE2A (NM_002599.3→NP_002590.1 (isoform 1); NM_001143839.2→NP_001137311.1 (isoform 2) and NM_001146209.1→NP_001139681.1 (isoform 3)); PDE3A (NM_000921.3→NP_000912.3); PDE3B (NM_000922.3→NP_000913.2); PDE4A (NM_001111307.1→NP_001104777.1 (isoform 1); NM_001111308.1→NP_001104778.1 (isoform 2); NM_001111309.1→NP_001104779.1 (isoform 3); NM_006202.2→NP_006193.1 (isoform 4)); PDE4B (NM_002600.3→NP_002591.2 (isoform 1); NM_001037341.1→NP_001032418.1 (isoform 1); NM_001037339.1→NP_001032416.1 (isoform 2); NM_001037340.1→NP_001032417.1 (isoform 3)); PDE4C-1 (NM_000923.3→NP 000914.2); PDE4C-2 (NM_001098819.1→NP_001092289.1); PDE4C-3 (NM_001098818.1→NP_001092288.1); PDE4D1 (NM_001197222.1→NP 001184151.1); PDE4D2 (NM_001197221.1→NP_001184150.1); PDE4D3 (NM_006203.4→NP_006194.2); PDE4D4 (NM_001104631.1→NP_001098101.1); PDE4D5 (NM_001197218.1→NP_001184147.1); PDE4D6 (NM_001197223.1→NP_001184152.1); PDE4D7 (NM_001165899.1→NP_001159371.1); PDE4D8 (NM_001197219.1→NP_001184148.1); PDE5A (NM_001083.3→NP_001074.2 (isoform 1); NM_033430.2→NP_236914.2 (isoform 2); NM_033437.3→NP_246273.2 (isoform 3)); PDE7A (NM_002603.2→NP_002594.1 (isoform a); NM_002604.2→NP_002595.1 (isoform b)); PDE7B (NM_018945.3→NP_061818.1); PDE8A (NM_002605.2→NP_002596.1 (isoform 1); NM_173454.1→NP 775656.1 (isoform 2)); PDE8B (NM_003719.3→NP_003710.1 (isoform 1); NM_001029854.2→NP_001025025.1 (isoform 2); NM_001029851.2→NP_001025022.1 (isoform 3); NM_001029853.2→NP_001025024.1 (isoform 4); NM_001029852.2→NP_001025023.1 (isoform 5)).

As discussed above, software programs for predicting siRNA sequences to inhibit the expression of a target protein are commercially available and find use. One program, siDESIGN from Dharmacon, Inc. (Lafayette, Colo.), permits predicting siRNAs for any nucleic acid sequence, and is available on the internet at dharmacon.com. Programs for designing siRNAs are also available from others, including Genscript (available on the internet at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

e. Other Anti-Inflammatory or Analgesic Agents

Other non-NSAID anti-inflammatory agents may also be co-administered with an agent that increases EETs (e.g., an inhibitor of sEH, an EET, an epoxygenated fatty acid, and mixtures thereof). For example, an agent that increases EETs (e.g., an inhibitor of sEH, an EET, an epoxygenated fatty acid, and mixtures thereof) can be co-administered with an agent that blocks binding of IL-6 to its cognate receptor (IL6R) or an agent that blocks binding of tumor necrosis factor alpha (TNFα) to its cognate receptor. Monoclonal antibodies directed against IL6 or IL6R and their potential impact for treatment of tumor-associated cachexia and as antitumoral agents are reviewed, e.g., by Weidle, et al., *Cancer Genomics Proteomics*. (2010) 7(6):287-302. Treatment with anti-TNF monoclonal antibodies (e.g., infliximab, adalimumab, and certolizumab pegol) has been shown to provide substantial benefit to patients through reductions in both localized and systemic expression of markers associated with inflammation. Alternatively, an agent that increases EETs (e.g., an inhibitor of sEH, an EET, an epoxygenated fatty acid, and mixtures thereof) may be co-administered with a soluble TNFα receptor (e.g., etanercept) and/or a soluble IL6 receptor. See, e.g., Sethi, et al., *Adv Exp Med Biol*. (2009) 647:37-51. In other embodiments, an agent that increases EETs (e.g., an inhibitor of sEH, an EET, an epoxygenated fatty acid, and mixtures thereof) is co-administered with glucosamine, chondroitin sulfate and/or polysulfated glycosaminoglycan (Adequan).

In various embodiments, the inhibitor of sEH is co-administered with an active agent selected from the group consisting of Gamma-aminobutyric Acid (GABA) analogs, N-methyl-D-aspartate receptor antagonists, opioids and sodium channel blockers, or analogs or pro-drugs thereof.

In various embodiments, the inhibitor of sEH is co-administered with a Gamma-aminobutyric Acid (GABA) analog, or analogs or pro-drugs thereof. Illustrative Gamma-aminobutyric Acid (GABA) analogs include without limitation gabapentin, pregabalin, and analogs or pro-drugs thereof. In some embodiments, one or both of the inhibitor of sEH and the Gamma-aminobutyric Acid (GABA) analog (e.g., gabapentin or pregabalin, or analogs or pro-drugs thereof), are administered in a sub-therapeutic amount.

In various embodiments, the inhibitor of sEH is co-administered with an N-methyl-D-aspartate receptor antagonist, or an analog or pro-drug thereof. Illustrative N-methyl-D-aspartate receptor antagonists include without limitation: AP5 (APV, R-2-amino-5-phosphonopentanoate); AP7 (2-amino-7-phosphonoheptanoic acid); CPPene (3-[(R)-2-carboxypiperazin-4-yl]-prop-2-enyl-1-phosphonic acid); Selfotel; Amantadine; Dextrallorphan; Dextromethorphan; Dextrorphan; Dizocilpine (MK-801); Eticyclidine; Gacyclidine; Ibogaine; Memantine; Methoxetamine; Nitrous oxide; Phencyclidine; Rolicyclidine; Tenocyclidine; Methoxydine; Tiletamine; Xenon; Neramexane; Eliprodil; Etoxadrol; Dexoxadrol; NEFA ((4aR,9aS)-N-Ethyl-4,4a,9,9a-tetrahydro-1H-fluoren-4a-amine); Remacemide; Delucemine; 8a-Phenyldecahydroquinoline (8A-PDHQ); Aptiganel (Cerestat, CNS-1102); Dexanabinol (HU-211); Rhynchophylline; and Ketamine.

In various embodiments, the inhibitor of sEH is co-administered with an opioid, or an analog or pro-drug thereof. Illustrative opioids include without limitation morphine, codeine, thebaine, heroin, hydromorphone, hydrocodone, oxycodone, oxymorphone, desomorphine, nicomorphine, dipropanoylmorphine, benzylmorphine, ethylmorphine, buprenorphine, fentanyl, pethidine, methadone, tramadol and dextropropoxyphene.

In various embodiments, the inhibitor of sEH is co-administered with a sodium channel blockers, or an analog or pro-drug thereof. Illustrative sodium channel blockers include without limitation tetrodotoxin (TTX), saxitoxin (STX), Benzocaine, Chloroprocaine, Cocaine, Cyclomethycaine, Dimethocaine/Larocaine, Piperocaine, Propoxycaine, Procaine/Novocaine, Proparacaine, Tetracaine/Amethocaine, Articaine, Bupivacaine, Cinchocaine/Dibucaine, Etidocaine, Levobupivacaine, Lidocaine/Lignocaine, Mepivacaine, Prilocaine, Ropivacaine, Trimecaine, and Lidocaine/prilocaine (EMLA), quinidine, procainamide, disopryamide, tocainide, mexiletine, flecainide, propafenone, moricizine, Carbamazepine, Phenytoin, Fosphenytoin, Oxcarbazepine, Lamotrigine, and Zonisamide.

In various embodiments, the one or more of the inhibitor of sEH and the active agent selected from the group consisting of Gamma-aminobutyric Acid (GABA) analogs, N methyl-D-aspartate receptor antagonists, opioids and sodium channel blockers, or analogs or pro-drugs thereof, are administered in a sub-therapeutic amount.

7. Formulation and Administration

In various embodiments of the compositions, the agent that increases EETs (e.g., an inhibitor of sEH, an EET, an epoxygenated fatty acid, and mixtures thereof) is administered as the sole active agent. In other embodiments, an anti-inflammatory agent and/or analgesic agent is combined with the agent that increases EETs (e.g., an inhibitor of sEH, an EET, an epoxygenated fatty acid, and mixtures thereof). The agent that increases EETs and the anti-inflammatory and/or analgesic agent can be formulated together (e.g., as a mixture) or separately. Optionally, the compositions comprise an anti-inflammatory agent and/or analgesic agent, and an inhibitor of sEH, or one or more EETs or an epoxide of EPA, of DHA, or one or more epoxides of both. In some embodiments, the composition is of an epoxide or EPA, of DHA, or epoxides of both, and an sEHi. The compositions can be prepared and administered in a wide variety of oral, parenteral and topical dosage forms. In preferred forms, compositions for use in the methods of the present invention can be administered orally, by injection, that is, intravenously, intramuscularly, intracutaneously, subcutaneously, intraduodenally, or intraperitoneally. The compositions can also be administered by inhalation, for example, intranasally. Additionally, the compositions can be administered transdermally. Accordingly, in some embodiments, the methods contemplate administration of compositions comprising a pharmaceutically acceptable carrier or excipient, an agent that increases EETs (e.g., an sEHi or a pharmaceutically acceptable salt of the inhibitor and, optionally, one or more EETs or epoxides of EPA or of DHA, or of both), and optionally an anti-inflammatory agent. In some embodiments, the methods comprise administration of an sEHi and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, N.Y.: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of sEHi by replacing the active ingredient or ingredient with an sEHi, with or without EETs. It is presumed that the person of skill is familiar with these various vehicles and preparations and they need not be described in detail herein.

The agent that increases EETs (e.g., an inhibitor of sEH, an EET, an epoxygenated fatty acid, and mixtures thereof), optionally mixed with an anti-inflammatory and/or analgesic agent, can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, Fla., 1997).

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of sEHi, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In various embodiments, sEHi can be mixed into a commercially available cream, Vanicream® (Pharmaceutical Specialties, Inc., Rochester, Minn.) comprising purified water, white petrolatum, ceteary1 alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents that inhibit sEH are topically administered (that is, whether by solid, liquid, lotion, gel, spray, etc.), in various embodiments they are administered at a dosage of about 0.01 mg to 10 mg per 10 $cm^2$. An exemplary dose for systemic administration of an inhibitor of sEH is from about 0.001 µg/kg to about 100 mg/kg body weight of the mammal. In various embodiments, dose and frequency of administration of an sEH inhibitor are selected to produce plasma concentrations within the range of 2.5 µM and 30 nM.

The agent that increases EETs (e.g., an inhibitor of sEH, an EET, an epoxygenated fatty acid, and mixtures thereof), optionally mixed with an anti-inflammatory and/or analgesic agent, can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount or a sub-therapeutic amount of one or more of the following: an sEH inhibitor, an EET, an epoxygenated fatty acid, can be administered in combination with an anti-inflammatory agent (e g., inhibitors of COX-1 or of -2, or both, or of a LOX enzyme). The dosage of the specific compounds depends on many factors that are well known to those skilled in the art. They include for example, the route of administration and the potency of the particular compound. An exemplary dose is from about 0.001 µg/kg to about 100 mg/kg body weight of the mammal. Doses of anti-inflammatory agents (e.g., NSAIDs, including inhibitors of COX-1, COX-2 and/or 5-LOX), phosphodiesterase inhibitors, Gamma-aminobutyric Acid (GABA) analogs (e.g., gabapentin and/or pregabalin), N-methyl-D-aspartate receptor antagonists, opioids and sodium channel blockers, or analogs or pro-drugs thereof are known in the art, and can be found, e.g., in the published literature and in reference texts, e.g., the Physicians' Desk Reference, 66th Ed., 2012, Thomson Healthcare or Brunton, et al., Goodman & Gilman's The Pharmacological Basis of Therapeutics, 12th edition, 2010, McGraw-Hill Professional). Because of the cooperative action between the agent that increases EETs (e.g., an sEH inhibitor, an EET, an epoxygenated fatty acid, and mixtures thereof) and the anti-inflammatory agent, one or both of the co-administered agents can be administered at a sub-therapeutic dose.

Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 12th Edition, 2010, supra; in a Physicians' Desk Reference (PDR), $65^{th}$ Edition, 2011; in *Remington: The Science and Practice of Pharmacy,* $21^{st}$ Ed., 2005, supra; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

EETs, EpDPEs, or EpETEs are unstable, and can be converted to the corresponding diols, in acidic conditions, such as those in the stomach. To avoid this, EETs, EpDPEs, or EpETEs can be administered intravenously or by injection. EETs, EpDPEs, or EpETEs intended for oral administration can be encapsulated in a coating that protects the compounds during passage through the stomach. For example, the EETs, EpDPEs, or EpETEs can be provided with a so-called "enteric" coating, such as those used for some brands of aspirin, or embedded in a formulation. Such enteric coatings and formulations are well known in the art. In some formulations, the compositions are embedded in a slow-release formulation to facilitate administration of the agents over time.

It is understood that, like all drugs, sEHis have half-lives defined by the rate at which they are metabolized by or excreted from the body, and that the sEHis will have a period following administration during which they will be present in amounts sufficient to be effective. If EETs, EpDPEs, or EpETEs are administered after the sEHi is administered, therefore, it is desirable that the EETs, EpDPEs, or EpETEs be administered during the period during which the sEHi will be present in amounts to be effective in delaying hydrolysis of the EETs, EpDPEs, or EpETEs. Typically, the EETs, EpDPEs, or EpETEs will be administered within 48 hours of administering an sEH inhibitor. Preferably, the EETs, EpDPEs, or EpETEs are administered within 24 hours of the sEHi, and even more preferably within 12 hours. In increasing order of desirability, the EETs, EpDPEs, or EpETEs are administered within 10, 8, 6, 4, 2, hours, 1 hour, or one half hour after administration of the inhibitor. When co-administered, the EETs, EpDPEs, or EpETEs are preferably administered concurrently with the sEHi.

It will be appreciated that the sEHis and, optionally, the EETs, EpDPEs, or EpETEs, do not need to be combined with the anti-inflammatory agent (e.g., COX-1 inhibitor, COX-2 inhibitor, LOX inhibitor, or COX/LOX inhibitor) or the analgesic agent. They can instead be administered separately. If the sEHis are administered separately (with or without EETs, EpDPEs, or EpETEs), they should be administered shortly before or concurrently with administration of the anti-inflammatory agent (e.g., COX-1 inhibitor, COX-2 inhibitor, LOX inhibitor, or COX/LOX inhibitor) or analgesic agent. If the sEHi is administered after administration of the anti-inflammatory agent (e.g., COX-1 inhibitor, COX-2 inhibitor, LOX inhibitor, or COX/LOX inhibitor) or analgesic agent, it should be administered as soon as possible after administration of the anti-inflammatory agent (e.g., COX-1 inhibitor, COX-2 inhibitor, LOX inhibitor, or COX/LOX inhibitor) or analgesic agent to maximize the cooperative action between the co-administered agents. Administration of the sEHi will still be beneficial even if it follows the anti-inflammatory agent (e.g., COX-1 inhibitor, COX-2 inhibitor, LOX inhibitor, or COX/LOX inhibitor) or analgesic agent by some time, however, so long as amounts of the anti-inflammatory agent (e.g., COX-1 inhibitor, COX-2 inhibitor, LOX inhibitor, or COX/LOX inhibitor) or analgesic agent are sufficient to inhibit the respective enzyme are still present.

8. Methods of Monitoring

A variety of methods can be employed in determining efficacy of therapeutic and/or prophylactic treatment of pain and/or inflammation with an agent that increases EETs, optionally in combination with an anti-inflammatory and/or analgesic agent. Generally, efficacy is the capacity to produce an effect without significant toxicity. Efficacy indicates that the therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment.

Efficacy of a treatment can be determined using a variety of methods, including pharmacological studies, diagnostic studies, predictive studies and prognostic studies. Examples of indicators of efficacy include but are not limited to patient response to stimulus (e.g., touching, pressure, temperature or weight-bearing), blood levels of $PGE_2$, blood pressure, heart rate, behavior assessment (e.g., level of activity, limb load distribution, kinematics, loss of laminitis stance, willingness to stand and walk without encouragement, eating). In various embodiments, efficacy can be determined by assigning a pain score, e.g., using a visual analog scale (VAS) or other known methods for quantifying pain in a non-human animal. See, e.g., Bufalari, et al., Veterinary Research Communications, 31(Suppl. 1), 55-58; Love, et al., Vet Anaesth Analg. (2011) 38(1):3-14; Viñuela-Fernandez, et al., Equine Vet J. (2011) 43(1):62-8; Ashley, et al., Equine Vet J. (2005) 37(6):565-75; Guillot, et al., J Vet Intern Med. (2011) 25(5):1050-6; Hielm-Björkman, et al., Am J Vet Res. (2011) 72(5):601-7; Brown, et al., J Am Vet Med Assoc. (2010) 237(1):66-70; and Brondani, et al., Am J Vet Res. (2011) 72(2):174-83. A lower pain score assigned after treatment with the agent that increases EETs indicates efficacy.

The methods of the present invention provide for detecting prevention, reduction, inhibition and/or reversal of painful and/or inflammatory conditions in a non-human mammal. A variety of methods can be used to monitor both therapeutic treatment for symptomatic patients and prophylactic treatment for asymptomatic patients.

Monitoring methods entail determining a baseline value of pain and/or inflammation in a patient before administering a dosage of the one or more agents that increase EETs, optionally in combination with an anti-inflammatory and/or analgesic agent, and comparing this with a value of pain and/or inflammation after treatment, respectively. The value can be based on one or more indicators of efficacy.

With respect to therapies using one or more agents that increase EETs, a significant decrease (i.e., greater than the typical margin of experimental error in repeat measurements of the same sample, expressed as one standard deviation from the mean of such measurements) in value of the pain and/or inflammation signals a positive treatment outcome (i.e., that administration of the one or more agents that increase EETs) has blocked or inhibited, or reduced progression of the painful and/or inflammatory condition).

In other methods, a control value of pain and/or inflammation (e.g., a mean and standard deviation) is determined from a control population of individuals who have undergone successful treatment with an agent that increases EETs). Measured values of pain and/or inflammation in a patient are compared with the control value. If the measured level in a patient is not significantly different (e.g., more than one standard deviation) from the control value, treatment can be discontinued. If the pain and/or inflammation levels in the patient are significantly above the control value, continued administration of the agent that increases EETs is warranted.

In other methods, a patient who is not presently receiving treatment but has undergone a previous course of treatment is monitored for symptoms and or indicators of pain and/or inflammation to determine whether a resumption of treatment is required. The measured value of pain and/or inflammation in the patient can be compared with a value of pain and/or inflammation previously achieved in the patient after a previous course of treatment. A significant increase in pain and/or inflammation relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after successfully undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase in pain and/or inflammation relative to the control level (i.e., more than a standard deviation) is an indicator that treatment should be resumed in a patient.

Where a tissue sample is evaluated, the tissue sample for analysis is can be blood, plasma, serum, mucous, tissue biopsy, and/or synovial fluid from the patient, as appropriate. Pain and/or inflammation can be detected using any method known in the art, e.g., visual observation of a biopsy by a qualified pathologist, or other visualization techniques, e.g., radiography, ultrasound, magnetic resonance imaging (MRI).

Further, the level of immune system activity in conjunction with pain and/or inflammation in a patient before administering a dosage of an agent that increases EETs can be compared with a value for immune system activity in conjunction with pain and/or inflammation after treatment, respectively.

EXAMPLES

The following examples are offered to illustrate, but not to limit the claimed invention.

Example 1

Use of a Soluble Epoxide Hydrolase Inhibitor as Adjunctive Analgesic in a Laminitic Horse A 4-year-old, 500 kg, female Thoroughbred horse was examined by the Veterinary Field Service of the UCDavis Veterinary Medical Teaching Hospital with the presenting complain of swollen on the left forelimb and reluctance to walk. The mare was reportedly found that morning unable to move, painful in both front feet and a rectal temperature of 38.6° C. Pertinent previous history included a moderate to severe lesion (44% tear) of the left forelimb superficial digital flexor tendon while on the racetrack 7 months prior. The mare was then donated to the UCDavis Center for Equine Health to be used as a research subject, and was subsequently enrolled in a stem cell study. The mare underwent computed tomography angiography followed by intraarterial regional limb perfusion of 99mTc-HMPAO labeled mesenchymal stem cells of the left forelimb. The cells were delivered via a catheter placed in the median artery at the level of the distal radius and the perfusion was performed without the use of a tourniquet. Swelling of the region of the left carpus and proximal region of the third metacarpal bone was noted in the immediate post-operative period. It resolved without obvious complications following treatment that included leg bandage, stall rest, and oral administration of phenylbutazone (1 g twice a day) for three days.

Physical examination findings included tachycardia (60 beats minute-1), tachypnea (40 breaths minute-1), increased digital pulses in both forelimbs, bilateral forelimb swelling in the region of the third metacarpal bones, focal swelling on the medial and lateral aspect of the left radius that appeared painful on palpation. The mare had symmetrical adequate muscling but was standing in a rocked back position and unable to walk without much encouragement. All other physical examination parameters were within normal reference limits. Orthogonal radiographic projections of the left and right front distal extremities revealed medial to lateral hoof imbalance bilaterally, mild dorsal hoof wall thickening bilaterally, with fracture of the dorso-distal aspect of the distal phalanx bilaterally, but no evidence of rotation or sinking Orthogonal and craniolateral-caudomedial oblique radiographic projections of the left radius revealed radial soft tissue swelling without evidence of osseous involvement. Irregularity of the caudodistal left radius likely represented remodeling secondary to previous trauma unlikely to be clinically significant. The changes in the distal extremities were suggestive of laminitis.

A clinical diagnosis of left forelimb cellulitis and bilateral forelimb laminitis was made. Initial therapy included cold hydrotherapy (once daily), flunixin meglumine (1 mg/kg, twice daily, IV), penicillin G procaine (PPG; 24,000 U/kg, twice daily, IM), gentamicin (3.5 mg/kg, once daily, IV). Soft Ride boots were applied bilaterally. A sweat stack wrap was placed on the left forelimb, and a standing sweat wrap was placed on the right, both containing furazone, dimethyl sulfoxide (DMSO) and epsom salts. This therapy was continued for the next four days (days 2, 3, 4 and 5), although the dose and route of administration of flunixin meglumine were changed (0.5 mg/kg, twice daily, PO) on days 4 and 5. Over this period, the cellulitis was improving and the mare appeared more comfortable until day 5, when it became increasingly more painful. Phenylbutazone (4 mg/kg, IV) was administered for pain relief and the therapy was changed such that flunixin meglumine and PPG were discontinued and phenylbutazone (4 mg/kg twice daily, PO), trimethoprim sulfamethoxazole (30 mg/kg twice daily, PO) and pentoxyphiline (11 mg/kg twice daily, PO) were instituted. On day 6, the mare became very painful (pain score 8.5/10 on visual analog scale, VAS; "0"=no pain and "10"=worst possible pain (Vinuela-Fernandez et al. 2011) and was standing but unwilling to walk. Although the cellulitis had improved significantly (almost not noticeable), the mare was displaying signs of laminitis in both forefeet. The hind feet also appeared to be slightly painful. Gabapentin (20 mg/kg twice daily, PO) was added to the treatment protocol.

The condition further deteriorated on day 7, with the mare spending most of the day laying down in lateral recumbency. It required much encouragement to stand up and, once standing, was unwilling to walk. At this time, systematic assessments of pain with the use of a VAS, as well as monitoring of blood pressure, heart and respiratory rates, and gastrointestinal sounds (Teixeira Neto et al. 2004) were instituted. Blood pressure was measured in triplicates, non-invasively with oscillometric technique (Cardell Model 9401 BP Monitor, Sham Veterinary Inc., Tampa, Fla.), with a tail cuff (width equal to 40% of the circumference of the base of the tail) and the horse in standing position (corrected for heart-tail height difference). Three individuals (two third year residents—equine surgery and anesthesia—and one board certified anesthesiologist) independently assessed the patient throughout the day taking into account changes in expression, demeanor, posture, stance and mobility. Two individuals (residents) were unaware of the identity and mechanism of action of the compound. An overall daily VAS score was then assigned. All assessments were done with the patient in the stall and the results are shown in FIG. 1. On day 7, the average VAS score was 9 out of 10 and blood pressure measurements revealed significant hypertension.

Figure 2:
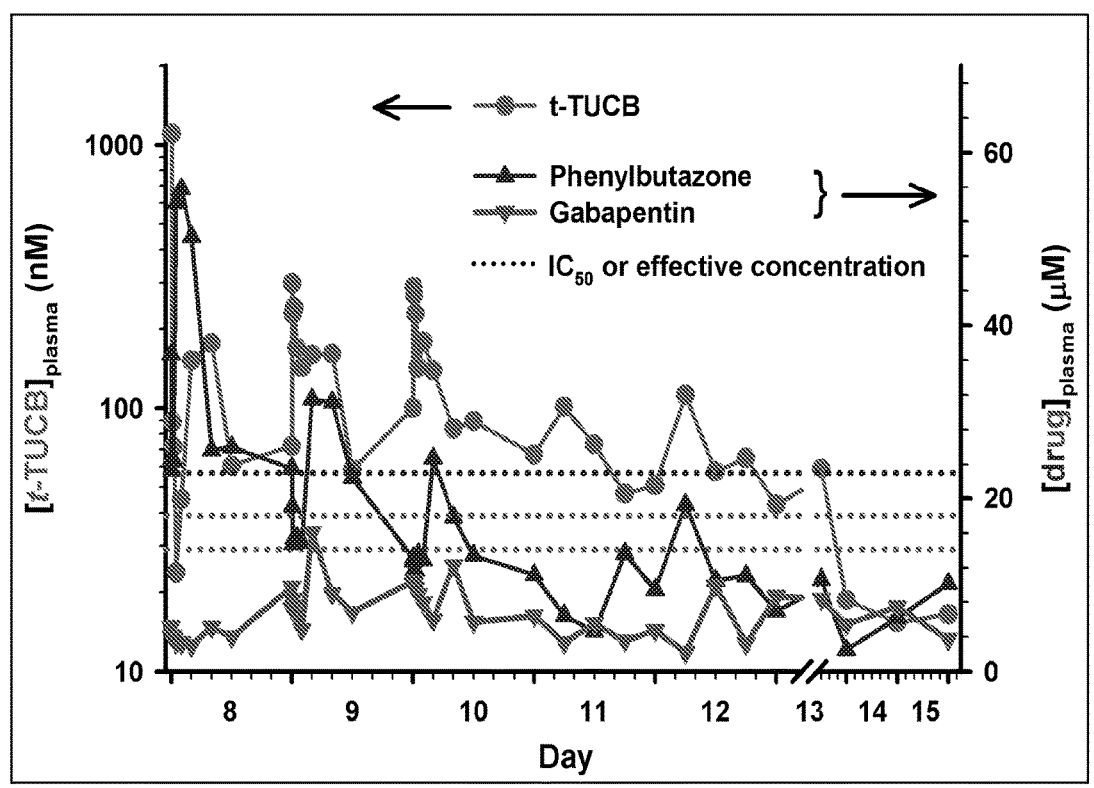
FIG. 2 illustrates plasma concentrations of the experimental drug inhibitor of soluble epoxide hydrolases t-TUCB (0.1 mg/kg SID, IV), phenylbutazone (3-4 mg/kg BID, PO) and gabapentin (20 mg/kg BID, PO) in one horse with pain due to laminitis.
Figure 3:
FIG. 3 illustrates the 4-year old, 500 kg Thoroughbred female horse diagnosed with severely painful bilateral forelimb laminitis and cellulitis on the left forelimb that was refractory to non-steroidal anti-inflammatory therapy before she received administration of the inhibitor of sEH, trans-4-{4-[3-(4-Trifluoromethoxy-phenyl)-ureido]-cyclohexyloxy}-benzoic acid (t-TUCB) (compound 1728). She was lying down most of the day and was reluctant to stand and to walk.
Figure 4:
FIG. 4 illustrates the 4-year old, 500 kg Thoroughbred female horse during her course of treatment receiving t-TUCB (compound 1728). The medication was administered once daily. Her pain level, movement, blood pressure, heart rate, respiratory rate, and intestinal function were monitored throughout the day. Furthermore, bloodwork was performed to monitor for adverse effects. t-TUCB (compound 1728) was administered early in the morning of day 8 and the patient spent most of that day standing on her feet instead of lying down. Her pain level decreased throughout the day, although was still high. In the next few days, the pain level subsided progressively (see daily pain scores in FIG. 1A) and the high blood pressure improved towards normal (see daily blood pressure measurements in FIG. 1B). At the same time, her stance pattern was more natural, and she was often resting one of the hind feet as is common in healthy horses. Horses with laminitis and pain in the front limbs assume a typical stance aimed at reducing weight in the front limbs. To accomplish this, the animal assumes a posture where the hind feet are moved forward, the head and neck are elevated and the front limbs are extended forward. Basically, the center of gravity is moved back and more weight is placed in the hind feet. The patient had this posture before administration of Compound 1728. This posture improved steadily after administration of t-TUCB (compound 1728). Once moving in the stall, she was progressively less and less reluctant to take steps.
Figure 5:
FIG. 5 illustrates the 4-year old, 500 kg Thoroughbred female horse 30 days after receiving t-TUCB (compound 1728). t-TUCB (compound 1728) was administered for a total of 5 days (days 8 to 12) and, given the sustained improvement, it was discontinued after day 12. The patient continued to do well and had a full clinical recovery. No signs of adverse effects were observed both from clinical exams and evaluation of blood work.
Figure 6:
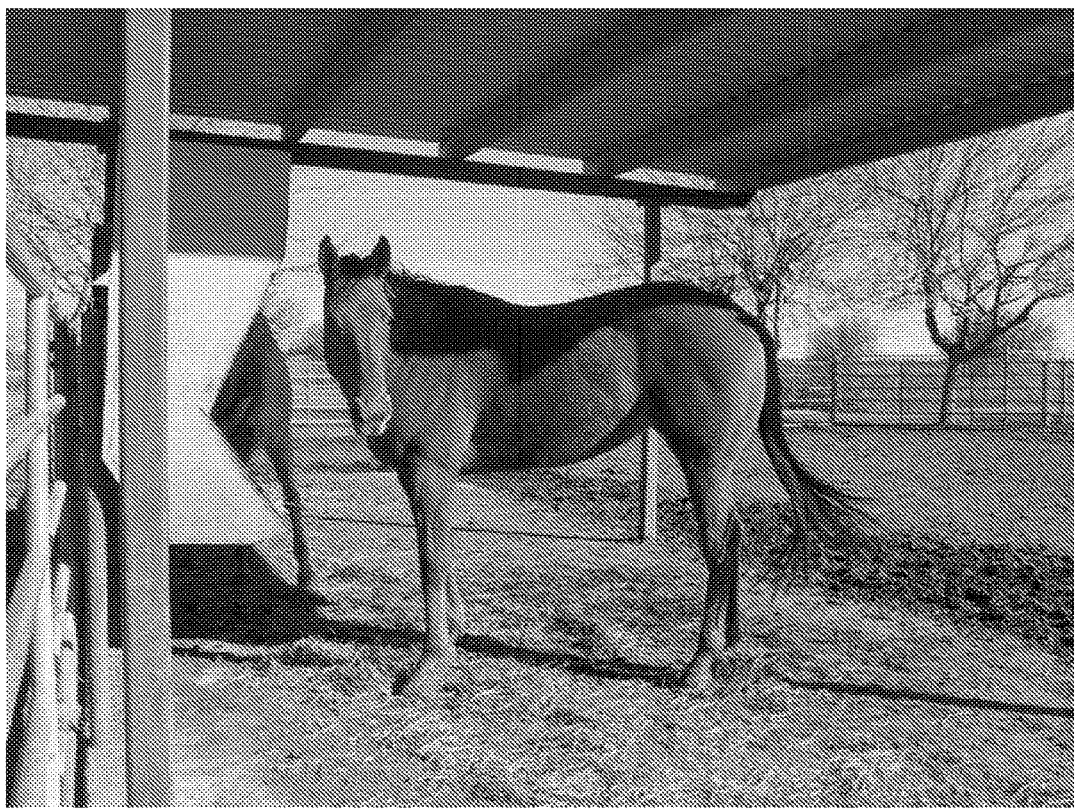
FIG. 6 illustrates the 4-year old, 500 kg Thoroughbred female horse 90 days after receiving t-TUCB (compound 1728).

Euthanasia was being considered at this stage for humane reasons coupled with technical and financial constraints. A decision was made to add an experimental drug, trans-4-{4-[3-(4-Trifluoromethoxy-phenyl)-ureido]-cyclohexyloxy}-benzoic acid (t-TUCB), to the treatment protocol. This drug has been shown to be a potent analgesic in classic rodent models of inflammatory and neuropathic pain (Inceoglu et al. 2006; Schmelzer et al. 2006; Inceoglu et al. 2007; Inceoglu et al. 2008; Morisseau et al. 2010; Wagner et al. 2011a; Wagner et al. 2011b), and is currently being investigated as a potential new analgesic in horses under approval by the Institutional Animal Care and Use Committee of the University of California-Davis. Dose (0.1 mg/kg) and frequency of administration (once daily) were selected to produce plasma concentrations within the range of approximately 2.5 µM (peak) and 30 nM (trough). Concentrations in this range are expected to be sufficient to inhibit the equine sEH in vivo on the basis of previous studies (Inceoglu et al. 2006; Morisseau et al. 2006; Inceoglu et al. 2008; Tsai et al. 2010; Ulu et al. 2011) and the in vitro potency against the equine sEH. The drug was dissolved in dimethyl sulfoxide (DMSO) to a final concentration of 10 mg/ml, filter-sterilized with 0.2 µm pore size sterilizing-grade membranes, and administered intravenously as a bolus by hand over a period of approximately one minute. To determine the plasma concentrations of t-TUCB, blood samples were collected from the opposite jugular vein just prior to t-TUCB administration (baseline), at 5, 15 and 30 minutes, and at 1, 2, 4, 8, 12 and 24 hours following each of the first three doses (days 8, 9 and 10), at 6, 12, 18 and 24 hours following each of the next two doses (days 11 and 12), and at 36, 48, 72 and 96 hours following the last dose (day 12). Plasma concentrations of phenylbutazone and gabapentin were determined in these same blood samples, but corresponded to slightly different time points since they were being administered one hour after (phenylbutazone) or five hours before (gabapentin) t-TUCB. The results are shown in FIG. 2. In addition, blood was also collected on days 8, 9, 10 and 13 for laboratory analyzes of complete blood cell count (CBC) and serum biochemistry (CHEM) and results are presented on Table 1.

TABLE 1

Hematology and serum biochemistry values at baseline (before the first dose on day 8) and after the first (day 9), second (day 10) and fifth (day 13) dose of an experimental new drug inhibitor of soluble epoxide hydrolases (t-TUCB 0.1 mg kg$^{-1}$ IV) as part of multimodal analgesic therapy in one horse with pain due to laminitis.

| TEST | Day 8 | Day 9 | Day 10 | Day 13 | Reference limits |
|---|---|---|---|---|---|
| HEMATOLOGY | | | | | |
| Red Blood Cells (M µL$^{-1}$) | 8.1 | 8.1 | 8.5 | 7.8 | 6.2-10.2 |
| Hemoglobin (g dL$^{-1}$) | 13.1 | 13.1 | 13.6 | 12.5 | 11.2-17.2 |
| Hematocrit (%) | 33.5 | 33.1 | 34.9 | 32.1 | 30-46 |
| Mcv (fL) | 41.2 | 40.9 | 41.1 | 40.9 | 37-53 |
| Mch (pg) | 16.1 | 16.2 | 16 | 15.9 | 14-20 |
| Mchc (g dL$^{-1}$) | 39.1 | 39.6 | 39 | 38.9 | 36-39 |
| Rdw (%) | 18.1 | 18 | 17.8 | 17.9 | 16-20 |
| Anisocytosis | Slight | Slight | Slight | Slight | — |
| Echinocytes | — | Few | Few | Few | — |
| White Blood Cells (/µL) | 9000 | 8170 | 11200 | 7320 | 5000-11600 |
| Neutrophils (/µL) | 5652 | 5245 | 8299 | 3967 | 3400-11900 |
| Lymphocytes (/µL) | 2943 | 2582 | 2498 | 3016 | 1600-5800 |
| Monophils (/µL) | 333 | 270 | 314 | 271 | 0-500 |
| Eosinophils (/µL) | 63 | 57 | 56 | 51 | 0-200 |
| Basophils (/µL) | 27 | 25 | 22 | 22 | 0-100 |
| Platelets (×10$^3$ µL$^{-1}$) | 250 | 231 | 257 | 251 | 100-225 |
| Plasma protein (g dL$^{-1}$) | 7 | 7 | 6.9 | 6.8 | 5.8-8.7 |
| Plasma fibrinogen (mg dL$^{-1}$) | 300 | 300 | 400 | 500 | 100-400 |
| Pp:Pf | 22 | 22 | 16 | 13 | — |
| BIOCHEMISTRY | | | | | |
| Creatinine (mg dL$^{-1}$) | 1 | 1.1 | 1.1 | 1.1 | 0.9-2.0 |
| Magnesium, Ionized (mmol L$^{-1}$) | 0.54 | 0.47 | 0.55 | 0.51 | 0.47-0.7 |
| Anion Gap (mmol L$^{-1}$) | 12 | 12 | 11 | 12 | 9-17 |
| Sodium (mmol L$^{-1}$) | 134 | 137 | 136 | 137 | 125-137 |
| Potassium (mmol L$^{-1}$) | 4.3 | 3.8 | 4 | 3.8 | 3.0-5.6 |
| Chloride (mmol L$^{-1}$) | 99 | 101 | 101 | 99 | 91-104 |
| Bicarbonate (mmol L$^{-1}$) | 27 | 28 | 28 | 30 | 23-32 |
| Phosphorus (mg dL$^{-1}$) | 3.3 | 3.7 | 2.7 | 3.4 | 2.1-4.7 |
| Calcium (mg dL$^{-1}$) | 12.9 | 12.4 | 12.5 | 12 | 11.4-14.1 |
| BUN (mg dL$^{-1}$) | 22 | 21 | 21 | 22 | 12-27 |
| Glucose (mg dL$^{-1}$) | 104 | 88 | 104 | 97 | 50-107 |
| Total Protein (g dL$^{-1}$) | 6.2 | 6.2 | 6.2 | 5.8 | 5.8-7.7 |
| Albumin (g dL$^{-1}$) | 3.3 | 3.3 | 3.4 | 3.1 | 2.7-4.2 |
| Globulin (g dL$^{-1}$) | 2.9 | 2.9 | 2.8 | 2.7 | 1.6-5.0 |
| AST (IU L$^{-1}$) | 506 | 489 | 459 | 358 | 168-494 |
| Creatine Kinase (IU L$^{-1}$) | 273 | 223 | 195 | 163 | 119-287 |
| Alkaline Phosphatase (IU L$^{-1}$) | 118 | 119 | 126 | 113 | 86-285 |
| GGT (IU L$^{-1}$) | 11 | 11 | 11 | 11 | 8-22 |
| Triglycerides (mg dL$^{-1}$) | 24 | 32 | 30 | 35 | 2-41 |
| Bilirubin Total (mg dL$^{-1}$) | 1.5 | 1.5 | 1.6 | 1.3 | 0.5-2.3 |
| Bilirubin Direct (mg dL$^{-1}$) | 0.2 | 0.1 | 0.1 | 0.1 | 0.2-0.6 |
| Bilirubin Indirect (mg dL$^{-1}$) | 1.3 | 1.4 | 1.5 | 1.2 | 1.7-3.6 |
| SDH-37 (IU L$^{-1}$) | 0 | 0 | 0 | 0 | 0-8 |
| Hemolysis Index | 21 | 77 | 43 | 23 | 2 |
| Icteric Index | 3 | 3 | 3 | 2 | — |
| Lipemic Index | 5 | 5 | 6 | 9 | — |

The first dose of t-TUCB was administered early in the morning of day 8. The mare spent majority of that day standing in the stall, was interested in surroundings, begun to walk spontaneously and was frequently looking out the front stall door. The average VAS pain score was 5.5. Hypertension was still present. Initial laboratory analyzes of CBC and CHEM revealed no significant changes after the first dose of t-TUCB. With these encouraging results, t-TUCB continued to be administered for four more days (days 9, 10, 11 and 12). In the following days, the mare continued to improve in expression, demeanor, posture, stance and mobility, which was reflected by lower VAS pain scores (FIG. 1A). As treatment progressed, the hypertension improved gradually towards normal physiologic values (FIG. 1B).

Daily plasma concentrations of t-TUCB were within the expected range, although it did not reach 2.5 µM and it fell below 30 nM on one occasion in the first day. The calculated volume of distribution, elimination half-life and clearance of t-TUCB for this horse were 1.22 ml/kg, 29.8 hr and 0.04 ml hr/kg, respectively. The highest and lowest measured plasma concentrations of phenylbutazone were 55 µM and 2 µM, and those of gabapentin were 18 µM and 1 µM. The true peaks of gabapentin were likely missed since the first blood sampling occurred five hours after dosing. This was due to the scheduled times for gabapentin administration and because the primary goal in this case was to determine the plasma concentrations of t-TUCB.

No adverse effects were observed both in the clinical exams and evaluation of blood work (Table 1). At 30 days follow-up the mare was normotensive and had no evidence of lameness. At 90 days, a few irregularities were apparent on the hoof wall, no episodes of lameness have been noticed.

Discussion

This case report is the first description of the successful use of the sEH inhibitor t-TUCB, as analgesic adjunct in a horse with laminitis. The horse was being treated for laminitis for seven days and, after an initial improvement, the condition deteriorated significantly. The severe pain was not responding to NSAIDs and gabapentin therapy. A remarkable reduction in pain scores occurred after pharmacological inhibition of sEH with t-TUCB. Notably, after being recumbent most of the previous day, the horse stood after the first dose of t-TUCB and was willing to walk, albeit somewhat reluctantly, in the stall and had good appetite. Inhibitors of sEH have been shown to be potent anti-inflammatory and analgesic agents in classic rodent models of both inflammatory and neuropathic pain (Inceoglu et al. 2006; Schmelzer et al. 2006; Inceoglu et al. 2007; Inceoglu et al. 2008; Morisseau et al. 2010; Wagner et al. 2011a; Wagner et al. 2011b). The observations in this horse with naturally occurring laminitis suggest that these compounds work not only in experimental models, but may have utility in the treatment of diseases associated with inflammation and pain. This notion is being tested in ongoing experiments. Preliminary data show that the concentration of several epoxides and respective diols derived from relevant long-chain fatty acids is changed in laminitic compared to healthy horses (unpublished data).

Inhibitors of sEH have been shown to be stronger anti-inflammatory and analgesics than coxibs or NSAIDs in rodent models of inflammatory pain (Inceoglu et al. 2007; Wagner et al. 2011b). Thus, it is not possible to ascertain the sole analgesic contribution of t-TUCB in the case reported here even though pain that was refractory to phenylbutazone and gabapentin promptly improved once the sEHi was administered. Interactions of t-TUCB with phenylbutazone, gabapentin and/or pentoxifylinne likely occurred. It is known that co-administration of NSAIDs and sEHis result in enhancement of antinociception (Schmelzer et al. 2006). Interestingly, measured phenylbutazone plasma levels were below its 80% maximal inhibitory concentration (IC80; ~23 µM) against COX-2 for most of the time. The IC80 rather than the IC50 value seems more suitable for NSAIDs evaluation, particularly since valid anti-inflammatory effects are achieved when COX-2 activity is 80% inhibited (Beretta et al. 2005). However, an additive or even a synergistic effect between t-TUCB and phenylbutazone could be responsible for the analgesic efficacy in this report.

The minimum effective analgesic plasma concentration of gabapentin in horses is unknown (Terry et al. 2010) although it was used successfully in one horse with neuropathic pain (Davis et al. 2007). Measured plasma concentrations in the horse of the present report were well below the concentration that has been associated with analgesia (~18 µM) in human volunteers (Eckhardt et al. 2000). There probably was a positive interaction with the phosphodiesterase inhibitor pentoxifylline since analgesia produced by sEHis is cyclic AMP (cAMP)-dependent, other phosphodiesterase inhibitors have been shown to increase EET concentrations (Inceoglu et al. 2011), and pentoxifylline itself may have analgesic effects in inflammatory and neuropathic pain states (Vale et al. 2004; Liu et al. 2007). Collectively, the above information corroborate with the conclusion that sEH inhibition with t-TUCB played a central role in the pain management of the horse of this report. The favorable interactions between sEHis and NSAIDs in the arachidonic acid cascade might allow for the use of lower doses of NSAIDs while maintaining efficacy and minimizing the risks of NSAID-associated side effects.

Drugs or techniques that provide complete control of nociception are not desirable in horses with laminitis because pain also has a protective function. It is important to prevent placement of excessive weight on the affected limb that could lead to destruction of the inflamed laminar tissue. Therefore, a useful analgesic would control maladaptive pain (i.e., hyperalgesia, allodynia) while maintaining some degree of adaptive pain (i.e., pain that is protective to the organism). In the case reported here, the pain scores dropped sharply with the inclusion of t-TUCB, but as in rodents the sEHi did not abolish all nociceptive input from the feet. Modulation of hyperalgesia and allodynia with the use of sEHis has been demonstrated in rodent models (Inceoglu et al. 2006; Schmelzer et al. 2006; Inceoglu et al. 2007; Inceoglu et al. 2008; Morisseau et al. 2010; Inceoglu et al. 2011; Wagner et al. 2011a; Wagner et al. 2011b). An analgesic that provides the above and is also able to arrest the progression of the disease would be highly desirable. In this context, pharmacologic inhibition of sEH fully prevented mortality in LPS-exposed mice by promoting inflammatory resolution as shown by reductions in plasma levels of pro-inflammatory cytokines and nitric oxide metabolites and increases in the synthesis of lipoxins (Schmelzer et al. 2005). As such, it is feasible that the improvement seen in this case of laminits resulted from nociceptive modulation via several mechanisms, and possibly also from arresting of the inflammatory events in laminar tissue. Future studies are warranted to test this hypothesis.

Because laminitis is a complex disease we cannot distinguish the comparative contributions of the different known biological effects of sEHi. However, laminitis presents as laminar inflammation and inflammatory pain transitioning into chronic and possibly neuropathic pain (Hood 1999; Driessen et al. 2010). The association of hypertension could have a number of causes including a response from pain itself. However, this complex disorder addresses the multiple advantages of sEHi in reducing hypertension, inflammation, inflammatory pain, neuropathic pain and toxicity associated with NSAIDs and COXIBs (Node et al. 1999; Yu et al. 2000; Schmelzer et al. 2005; Inceoglu et al. 2006; Schmelzer et al. 2006; Chiamvimonvat et al. 2007; Inceoglu et al. 2007; Inceoglu et al. 2008; Imig & Hammock 2009; Revermann 2010; Wagner et al. 2011a).

No undesirable effects could be detected in the horse of this report. To date, no overt adverse effects associated with sEH inhibition have been observed in studies in rodents (Inceoglu et al. 2006; Schmelzer et al. 2006; Inceoglu et al. 2007; Inceoglu et al. 2008; Morisseau et al. 2010) dogs (Tsai et al. 2010), and non-human primates (Ulu et al. 2011) even when co-administered with NSAIDs (Schmelzer et al. 2006). In fact, sEH inhibitors appear to have a remarkable sparing effect in the analgesic action of NSAIDs (Schmelzer et al. 2006), suggesting that lower effective doses of NSAIDs could be used thus minimizing risk of undesirable side effects.

In conclusion, inhibition of sEH with t-TUCB was associated with a significant improvement in pain scores in one horse with laminitis whose pain was refractory to the standard of care therapy. No adverse effects were noticed. Future studies evaluating the analgesic and protective effects of these compounds in painful inflammatory diseases in animals are warranted.

REFERENCES

Belknap J K, Giguere S, Pettigrew A et al. (2007) Lamellar pro-inflammatory cytokine expression patterns in laminitis at the developmental stage and at the onset of lameness: innate vs. adaptive immune response. Equine Vet J 39, 42-47.

Beretta C, Garavaglia G, Cavalli M (2005) COX-1 and COX-2 inhibition in horse blood by phenylbutazone, flunixin, carprofen and meloxicam: an in vitro analysis. Pharmacol Res 52, 302-306.

Chiamvimonvat N, Ho C M, Tsai H J et al. (2007) The soluble epoxide hydrolase as a pharmaceutical target for hypertension. J Cardiovasc Pharmacol 50, 225-237.

Davis J L, Posner L P, Elce Y (2007) Gabapentin for the treatment of neuropathic pain in a pregnant horse. J Am Vet Med Assoc 231, 755-758.

Decker M, Arand M, Cronin A (2009) Mammalian epoxide hydrolases in xenobiotic metabolism and signalling. Arch Toxicol 83, 297-318.

Driessen B, Bauquier S H, Zarucco L (2010) Neuropathic pain management in chronic laminitis. Vet Clin North Am Equine Pract 26, 315-337.

Eckhardt K, Ammon S, Hofmann U et al. (2000) Gabapentin enhances the analgesic effect of morphine in healthy volunteers. Anesth Analg 91, 185-191.

Hood D M (1999) The pathophysiology of developmental and acute laminitis. Vet Clin North Am Equine Pract 15, 321-343.

Hood D M, Grosenbaugh D A, Mostafa M B et al. (1993) The role of vascular mechanisms in the development of acute equine laminitis. J Vet Intern Med 7, 228-234.

Hwang S H, Tsai H J, Liu J Y et al. (2007) Orally bioavailable potent soluble epoxide hydrolase inhibitors. J Med Chem 50, 3825-3840.

Imig J D, Hammock B D (2009) Soluble epoxide hydrolase as a therapeutic target for cardiovascular diseases. Nat Rev Drug Discov 8, 794-805.

Inceoglu B, Jinks S L, Schmelzer K R et al. (2006) Inhibition of soluble epoxide hydrolase reduces LPS-induced thermal hyperalgesia and mechanical allodynia in a rat model of inflammatory pain. Life Sci 79, 2311-2319.

Inceoglu B, Jinks S L, Ulu A et al. (2008) Soluble epoxide hydrolase and epoxyeicosatrienoic acids modulate two distinct analgesic pathways. Proc Natl Acad Sci USA 105, 18901-18906.

Inceoglu B, Schmelzer K R, Morisseau C et al. (2007) Soluble epoxide hydrolase inhibition reveals novel biological functions of epoxyeicosatrienoic acids (EETs). Prostaglandins Other Lipid Mediat 82, 42-49.

Inceoglu B, Wagner K, Schebb N H et al. (2011) Analgesia mediated by soluble epoxide hydrolase inhibitors is dependent on cAMP. Proc Natl Acad Sci USA 108, 5093-5097.

Jones E, Vinuela-Fernandez I, Eager R A et al. (2007) Neuropathic changes in equine laminitis pain. Pain 132, 321-331.

Lakritz J, Winder B S, Noorouz-Zadeh J et al. (2000) Hepatic and pulmonary enzyme activities in horses. Am J Vet Res 61, 152-157.

Liu J, Feng X, Yu M et al. (2007) Pentoxifylline attenuates the development of hyperalgesia in a rat model of neuropathic pain. Neurosci Lett 412, 268-272.

Moalem G, Tracey D J (2006) Immune and inflammatory mechanisms in neuropathic pain. Brain Res Rev 51, 240-264.

Morisseau C, Hammock B D (2005) Epoxide hydrolases: mechanisms, inhibitor designs, and biological roles. Annu Rev Pharmacol Toxicol 45, 311-333.

Morisseau C, Hammock B D (2008) Gerry Brooks and epoxide hydrolases: four decades to a pharmaceutical. Pest Manag Sci 64, 594-609.

Morisseau C, Inceoglu B, Schmelzer K et al. (2010) Naturally occurring monoepoxides of eicosapentaenoic acid and docosahexaenoic acid are bioactive antihyperalgesic lipids. J Lipid Res 51, 3481-3490.

Morisseau C, Newman J W, Tsai H J et al. (2006) Peptidyl-urea based inhibitors of soluble epoxide hydrolases. Bioorg Med Chem Lett 16, 5439-5444.

Murakami M (2011) Lipid mediators in life science. Exp Anim 60, 7-20.

Node K, Huo Y, Ruan X et al. (1999) Anti-inflammatory properties of cytochrome P450 epoxygenase-derived eicosanoids. Science 285, 1276-1279.

Parks A, O'Grady S E (2003) Chronic laminitis: current treatment strategies. Vet Clin North Am Equine Pract 19, 393-416.

Peroni J F, Moore J N, Noschka E et al. (2006) Predisposition for venoconstriction in the equine laminar dermis: implications in equine laminitis. J Appl Physiol 100, 759-763.

Revermann M (2010) Pharmacological inhibition of the soluble epoxide hydrolase-from mouse to man. Curr Opin Pharmacol 10, 173-178.

Schmelzer K R, Inceoglu B, Kubala L et al. (2006) Enhancement of antinociception by coadministration of nonsteroidal anti-inflammatory drugs and soluble epoxide hydrolase inhibitors. Proc Natl Acad Sci USA 103, 13646-13651.

Schmelzer K R, Kubala L, Newman J W et al. (2005) Soluble epoxide hydrolase is a therapeutic target for acute inflammation. Proc Natl Acad Sci USA 102, 9772-9777.

Sumano Lopez H, Hoyas Sepulveda M L, Brumbaugh G W (1999) Pharmacologic and alternative therapies for the horse with chronic laminitis. Vet Clin North Am Equine Pract 15, 495-516.

Taylor P M, Pascoe P J, Mama K R (2002) Diagnosing and treating pain in the horse. Where are we today? Vet Clin North Am Equine Pract 18, 1-19.

Teixeira Neto F J, McDonell W N, Black W D et al. (2004) Effects of glycopyrrolate on cardiorespiratory function in horses anesthetized with halothane and xylazine. Am J Vet Res 65, 456-463.

Terry R L, McDonnell S M, Van Eps A W et al. (2010) Pharmacokinetic profile and behavioral effects of gabapentin in the horse. J Vet Pharmacol Ther 33, 485-494.

Tokuyama S, Nakamoto K (2011) Unsaturated Fatty acids and pain. Biol Pharm Bull 34, 1174-1178.

Tsai H J, Hwang S H, Morisseau C et al. (2010) Pharmacokinetic screening of soluble epoxide hydrolase inhibitors in dogs. Eur J Pharm Sci 40, 222-238.

Ulu A, Appt S, Morisseau C et al. (2011) Pharmacokinetics and in vivo potency of soluble epoxide hydrolase inhibitors in cynomolgus monkeys. Br J Pharmacol.

Vale M L, Benevides V M, Sachs D et al. (2004) Antihyperalgesic effect of pentoxifylline on experimental inflammatory pain. Br J Pharmacol 143, 833-844.

Vinuela-Fernandez I, Jones E, Chase-Topping M E et al. (2011) Comparison of subjective scoring systems used to evaluate equine laminitis. Vet J 188, 171-177.

Wagner K, Inceoglu B, Gill S S et al. (2011a) Epoxygenated fatty acids and soluble epoxide hydrolase inhibition: novel mediators of pain reduction. J Agric Food Chem 59, 2816-2824.

Wagner K, Inceoglu B, Hammock B D (2011b) Soluble epoxide hydrolase inhibition, epoxygenated fatty acids and nociception. Prostaglandins Other Lipid Mediat 96, 76-83.

Yu Z, Xu F, Huse L M et al. (2000) Soluble epoxide hydrolase regulates hydrolysis of vasoactive epoxyeicosatrienoic acids. Circ Res 87, 992-998.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of ameliorating or delaying the progression and/or reversing the progression of laminitis in an equine in need thereof, comprising administering to the equine an effective amount of trans-4-{4[3-(4-Trifluoromethoxy-phenyl)-ureido]-cyclohexyloxyl-benzoic acid (t-TUCB; compound 1728).

2. The method of claim 1, wherein said equine had previously been treated with a non-steroidal anti-inflammatory drug (NSAID) that did not prevent ameliorate, delay or reverse progression of the laminitis.

* * * * *

SEQUENCE LISTING

```
<160> NUMBER OF SEQ ID NOS: 38

<210> SEQ ID NO 1
<211> LENGTH: 554
<212> TYPE: PRT
<213> ORGANISM: Homo sapiens
<220> FEATURE:
<223> OTHER INFORMATION: Human soluble epoxide hydrolase (sEH)

<400> SEQUENCE: 1

Met Thr Leu Arg Gly Ala Val Phe Asp Leu Asp Gly Val Leu Ala Leu
1               5                   10                  15

Pro Ala Val Phe Gly Val Leu Gly Arg Thr Glu Glu Ala Leu Ala Leu
                20                  25                  30

Pro Arg Gly Leu Leu Asn Asp Ala Phe Gln Lys Gly Gly Pro Glu Gly
            35                  40                  45

Ala Thr Thr Arg Leu Met Lys Gly Glu Ile Thr Leu Ser Gln Trp Ile
        50                  55                  60

Pro Leu Met Glu Glu Asn Cys Arg Lys Cys Ser Glu Thr Ala Lys Val
65                  70                  75                  80

Cys Leu Pro Lys Asn Phe Ser Ile Lys Glu Ile Phe Asp Lys Ala Ile
                85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
    210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Trp Pro Ala Val Cys Leu Cys His Gly Phe Pro Glu Ser Trp Tyr Ser
            260                 265                 270
```

```
Trp Arg Tyr Gln Ile Pro Ala Leu Ala Gln Ala Gly Tyr Arg Val Leu
        275                 280                 285
Ala Met Asp Met Lys Gly Tyr Gly Glu Ser Ser Ala Pro Pro Glu Ile
    290                 295                 300
Glu Glu Tyr Cys Met Glu Val Leu Cys Lys Glu Met Val Thr Phe Leu
305                 310                 315                 320
Asp Lys Leu Gly Leu Ser Gln Ala Val Phe Ile Gly His Asp Trp Gly
                325                 330                 335
Gly Met Leu Val Trp Tyr Met Ala Leu Phe Tyr Pro Glu Arg Val Arg
            340                 345                 350
Ala Val Ala Ser Leu Asn Thr Pro Phe Ile Pro Ala Asn Pro Asn Met
        355                 360                 365
Ser Pro Leu Glu Ser Ile Lys Ala Asn Pro Val Phe Asp Tyr Gln Leu
    370                 375                 380
Tyr Phe Gln Glu Pro Gly Val Ala Glu Ala Glu Leu Glu Gln Asn Leu
385                 390                 395                 400
Ser Arg Thr Phe Lys Ser Leu Phe Arg Ala Ser Asp Glu Ser Val Leu
                405                 410                 415
Ser Met His Lys Val Cys Glu Ala Gly Gly Leu Phe Val Asn Ser Pro
            420                 425                 430
Glu Glu Pro Ser Leu Ser Arg Met Val Thr Glu Glu Glu Ile Gln Phe
        435                 440                 445
Tyr Val Gln Gln Phe Lys Lys Ser Gly Phe Arg Gly Pro Leu Asn Trp
    450                 455                 460
Tyr Arg Asn Met Glu Arg Asn Trp Lys Trp Ala Cys Lys Ser Leu Gly
465                 470                 475                 480
Arg Lys Ile Leu Ile Pro Ala Leu Met Val Thr Ala Glu Lys Asp Phe
                485                 490                 495
Val Leu Val Pro Gln Met Ser Gln His Met Glu Asp Trp Ile Pro His
            500                 505                 510
Leu Lys Arg Gly His Ile Glu Asp Cys Gly His Trp Thr Gln Met Asp
        515                 520                 525
Lys Pro Thr Glu Val Asn Gln Ile Leu Ile Lys Trp Leu Asp Ser Asp
    530                 535                 540
Ala Arg Asn Pro Pro Val Val Ser Lys Met
545                 550

<210> SEQ ID NO 2
<211> LENGTH: 1665
<212> TYPE: DNA
<213> ORGANISM: Homo sapiens
<220> FEATURE:
<223> OTHER INFORMATION: Human soluble epoxide hydrolase (sEH)

<400> SEQUENCE: 2
atgacgctgc gcggcgccgt cttcgacctt gacggggtgc tggcgctgcc agcggtgttc      60
ggcgtcctcg gccgcacgga ggaggccctg cgcgctgccca gaggacttct gaatgatgct     120
ttccagaaag ggggaccaga gggtgccact acccggctta tgaaaggaga gatcacactt     180
tcccagtgga taccactcat ggaagaaaac tgcaggaagt gctccgagac cgctaaagtc     240
tgcctcccca gaatttctc cataaaagaa atctttgaca aggcgatttc agccagaaag      300
atcaaccgcc ccatgctcca ggcagctctc atgctcagga gaaaggatt cactactgcc      360 atcctcacca cacctggct ggacgaccgt gctgagagag atggcctggc ccagctgatg      420
```

```
tgtgagctga agatgcactt tgacttcctg atagagtcgt gtcaggtggg aatggtcaaa      480
cctgaacctc agatctacaa gtttctgctg gacaccctga aggccagccc cagtgaggtc      540
gttttttggg atgacatcgg ggctaatctg aagccagccc gtgacttggg aatggtcacc      600
atcctggtcc aggacactga cacggccctg aaagaactgg agaaagtgac cggaatccag      660
cttctcaata ccccggcccc tctgccgacc tcttgcaatc caagtgacat gagccatggg      720
tacgtgacag taaagcccag ggtccgtctg cattttgtgg agctgggctg gcctgctgtg      780
tgcctctgcc atggatttcc cgagagttgg tattcttgga ggtaccagat ccctgctctg      840
gcccaggcag gttaccgggt cctagctatg gacatgaaag ctatggagag tcatctgct       900 cctcccgaaa tagaagaata ttgcatggaa gtgttatgta aggagatggt aaccttcctg      960
gataaactgg gcctctctca agcagtgttc attggccatg actggggtgg catgctggtg      1020
tggtacatgg ctctcttcta ccccgagaga gtgagggcgg tggccagttt gaatactccc      1080
ttcataccag caaatcccaa catgtcccct ttggagagta tcaaagccaa cccagtattt      1140
gattaccagc tctacttcca agaaccagga gtggctgagc tgaactggaa acagaacctg      1200
agtcggactt tcaaaagcct cttcagagca agcgatgaga gtgttttatc catgcataaa      1260
gtctgtgaag cgggaggact ttttgtaaat agcccagaag agcccagcct cagcaggatg      1320
gtcactgagg aggaaatcca gttctatgtg cagcagttca agaagtctgg tttcagaggt      1380
cctctaaact ggtaccgaaa catggaaagg aactggaagt gggcttgcaa agcttggga       1440 cggaagatcc tgattccggc cctgatggtc acggcggaga aggacttcgt gctcgttcct      1500
cagatgtccc agcacatgga ggactggatt ccccacctga aaaggggaca cattgaggac      1560
tgtgggcact ggacacagat ggacaagcca accgaggtga atcagatcct cattaagtgg      1620
ctggattctg atgcccggaa cccaccggtg gtctcaaaga tgtag                      1665
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) target sequence

<400> SEQUENCE: 3
cagtgttcat tggccatgac tgg                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) sense-small
      interfering RNA (siRNA)
<220> FEATURE:
<223> OTHER INFORMATION: Description of Combined DNA/RNA Molecule:
      Synthetic soluble epoxide hydrolase (sEH) sense-small
      interfering RNA (siRNA)

<400> SEQUENCE: 4
guguucauug gccaugacut t                                                21

<210> SEQ ID NO 5
<211> LENGTH: 21
<212> TYPE: DNA
<213> ORGANISM: Artificial Sequence
<220> FEATURE:

<223> OTHER INFORMATION: Description of Artificial Sequence: Synthetic
       soluble epoxide hydrolase (sEH) antisense-small
       interfering RNA (siRNA)
<220> FEATURE:
<223> OTHER INFORMATION: Description of Combined DNA/RNA Molecule:
       Synthetic soluble epoxide hydrolase (sEH) antisense-small
       interfering RNA (siRNA)

<400> SEQUENCE: 5
agucauggcc aaugaacact t                                             21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
       soluble epoxide hydrolase (sEH) target sequence

<400> SEQUENCE: 6
gaaaggctat ggagagtcat ctg                                           23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
       soluble epoxide hydrolase (sEH) sense-small
       interfering RNA (siRNA)
<220> FEATURE:
<223> OTHER INFORMATION: Description of Combined DNA/RNA Molecule:
       Synthetic soluble epoxide hydrolase (sEH) sense-small
       interfering RNA (siRNA)

<400> SEQUENCE: 7
aaggcuaugg agagucauct t                                             21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
       soluble epoxide hydrolase (sEH) antisense-small
       interfering RNA (siRNA)
<220> FEATURE:
<223> OTHER INFORMATION: Description of Combined DNA/RNA Molecule:
       Synthetic soluble epoxide hydrolase (sEH) antisense-small
       interfering RNA (siRNA)

<400> SEQUENCE: 8
gaugacucuc cauagccuut t                                             21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
       soluble epoxide hydrolase (sEH) target sequence

<400> SEQUENCE: 9
aaaggctatg gagagtcatc tgc                                           23

<210> SEQ ID NO 10
<211> LENGTH: 21
<212> TYPE: DNA
<213> ORGANISM: Artificial Sequence

```
<220> FEATURE:
<223> OTHER INFORMATION: Description of Artificial Sequence: Synthetic
      soluble epoxide hydrolase (sEH) sense-small interfering
      RNA (siRNA)
<220> FEATURE:
<223> OTHER INFORMATION: Description of Combined DNA/RNA Molecule:
      Synthetic soluble epoxide hydrolase (sEH) sense-small interfering
      RNA (siRNA)

<400> SEQUENCE: 10
aggcuaugga gagucaucut t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) antisense-small
      interfering RNA (siRNA)
<220> FEATURE:
<223> OTHER INFORMATION: Description of Combined DNA/RNA Molecule:
      Synthetic soluble epoxide hydrolase (sEH) antisense-small
      interfering RNA (siRNA)

<400> SEQUENCE: 11
agaugacucu ccauagccut t                                              21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) target sequence

<400> SEQUENCE: 12
caagcagtgt tcattggcca tga                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) sense-small interfering
      RNA (siRNA)
<220> FEATURE:
<223> OTHER INFORMATION: Description of Combined DNA/RNA Molecule:
      Synthetic soluble epoxide hydrolase (sEH) sense-small interfering
      RNA (siRNA)

<400> SEQUENCE: 13
agcaguguuc auuggccaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) antisense-small
      interfering RNA (siRNA)
<220> FEATURE:
<223> OTHER INFORMATION: Description of Combined DNA/RNA Molecule:
      Synthetic soluble epoxide hydrolase (sEH) antisense-small
      interfering RNA (siRNA)

<400> SEQUENCE: 14
auggccaaug aacacugcut t                                              21
```

```
<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) target sequence

<400> SEQUENCE: 15
cagcacatgg aggactggat tcc                                              23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) sense-small interfering
      RNA (siRNA)
<220> FEATURE:
<223> OTHER INFORMATION: Description of Combined DNA/RNA Molecule:
      Synthetic soluble epoxide hydrolase (sEH) sense-small interfering
      RNA (siRNA)

<400> SEQUENCE: 16
gcacauggag gacuggauut t                                                21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) antisense-small
      interfering RNA (siRNA)
<220> FEATURE:
<223> OTHER INFORMATION: Description of Combined DNA/RNA Molecule:
      Synthetic soluble epoxide hydrolase (sEH) antisense-small
      interfering RNA (siRNA)

<400> SEQUENCE: 17
aauccagucc uccaugugct t                                                21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      short spacer linking sense siRNA to reverse
      complementary antisense siRNA

<400> SEQUENCE: 18 ttcaagaga                                                               9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) target sequence

<400> SEQUENCE: 19
cagtgttcat tggccatgac tgg                                              23
```

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) sense strand

<400> SEQUENCE: 20
gatccccgtg ttcattggcc atgactttca agagaagtca tggccaatga acacttttt       59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) antisense strand

<400> SEQUENCE: 21
agctaaaaag tgttcattgg ccatgacttc tcttgaaagt catggccaat gaacacggg       59

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) target sequence

<400> SEQUENCE: 22
gaaaggctat ggagagtcat ctg                                              23

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering  RNA (siRNA) sense strand

<400> SEQUENCE: 23
gatccccaag gctatggaga gtcatcttca agagagatga ctctccatag cctttttt       59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering  RNA (siRNA) antisense strand

<400> SEQUENCE: 24
agctaaaaaa aggctatgga gagtcatctc tcttgaagat gactctccat agccttggg       59

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering  RNA (siRNA) target sequence

<400> SEQUENCE: 25
aaaggctatg gagagtcatc tgc    23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) sense strand

<400> SEQUENCE: 26
gatccccagg ctatggagag tcatctttca agagaagatg actctccata gccttttt    59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) antisense strand

<400> SEQUENCE: 27
agctaaaaaa ggctatggag agtcatcatc tcttgaaaga tgactctcca tagcctggg    59

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) target sequence

<400> SEQUENCE: 28
caagcagtgt tcattggcca tga    23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) sense strand

<400> SEQUENCE: 29
gatccccagc agtgttcatt ggccatttca agagaatggc caatgaacac tgcttttt    59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) antisense strand

<400> SEQUENCE: 30
agctaaaaaa gcagtgttca ttggccattc tcttgaaatg gccaatgaac actgctggg    59

<210> SEQ ID NO 31
<211> LENGTH: 23
<212> TYPE: DNA
<213> ORGANISM: Artificial Sequence

```
<220> FEATURE:
<223> OTHER INFORMATION: Description of Artificial Sequence: Synthetic
      soluble epoxide hydrolase (sEH) short hairpin
      small interfering RNA (siRNA) target sequence

<400> SEQUENCE: 31
cagcacatgg aggactggat tcc                                          23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) sense strand

<400> SEQUENCE: 32
gatccccgca catggaggac tggattttca agagaaatcc agtcctccat gtgcttttt   59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      soluble epoxide hydrolase (sEH) short hairpin
      small interfering RNA (siRNA) antisense strand

<400> SEQUENCE: 33
agctaaaaag cacatggagg actggatttc tcttgaaaat ccagtcctcc atgtgcggg   59

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 34
uguccagugc ccacaguccu                                              20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 35
uucccaccug acacgacucu                                              20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 36
guucagccuc agccacuccu                                              20

<210> SEQ ID NO 37
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 37
aguccucccg cuucacaga                                                    19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      soluble epoxide hydrolase (sEH) antisense sequence

<400> SEQUENCE: 38
gcccacuucc aguccuuuc c                                                  21
```